United States Patent
Coolbaugh et al.

[11] Patent Number: 5,773,524
[45] Date of Patent: Jun. 30, 1998

[54] EPOXIDIZED LIQUID ELASTOMERIC COPOLYMERS

[75] Inventors: Thomas S. Coolbaugh; Frederick C. Loveless, both of Yardley, Pa.; Demetreos N. Matthews, Ewing; Leslie R. Rudnick, Lawrenceville, both of N.J.

[73] Assignee: Mobil Oil Corporation, Fairfax, Va.

[21] Appl. No.: 514,200

[22] Filed: Aug. 11, 1995

Related U.S. Application Data

[60] Continuation-in-part of Ser. No. 382,814, Feb. 3, 1995, Pat. No. 5,545,783, which is a division of Ser. No. 179,051, Jan. 7, 1994, Pat. No. 5,387,730, which is a division of Ser. No. 992,341, Dec. 17, 1992, Pat. No. 5,288,937, which is a continuation of Ser. No. 907,959, Aug. 6, 1992, Pat. No. 5,210,359, which is a division of Ser. No. 466,135, Jan. 16, 1990, Pat. No. 5,149,895.

[51] Int. Cl.$^6$ ............................ C08F 36/14; C08F 236/14
[52] U.S. Cl. .................... 525/332.8; 525/331.9; 525/332.9; 525/333.1
[58] Field of Search .................. 525/331.9, 332.8, 525/332.9, 333.1

[56] References Cited

U.S. PATENT DOCUMENTS

| | | | |
|---|---|---|---|
| 3,448,174 | 6/1969 | Loveless et al. | 260/878 |
| 4,879,349 | 11/1989 | Hoxmeier | 525/332.8 |
| 5,187,236 | 2/1993 | Coolbaugh et al. | 525/314 |
| 5,229,464 | 7/1993 | Erickson et al. | 525/314 |
| 5,247,026 | 9/1993 | Erickson et al. | 525/314 |
| 5,446,104 | 8/1995 | Handlin, Jr. et al. | 525/314 |

FOREIGN PATENT DOCUMENTS

| | | |
|---|---|---|
| 0315280 | 5/1989 | European Pat. Off. |
| 3-28729 | 7/1989 | Japan |

OTHER PUBLICATIONS

Falk, Journal of Polymer Science: Part A–1, vol. 9, 2617–2623 (1971).
Falk, Die Angewandte Chemie 21 (1972) 17–23 (No. 236).
Mohajer et al., Polymer, 1982, vol. 23 Sep., 1523–1535.

*Primary Examiner*—Robert E. Sellers
*Attorney, Agent, or Firm*—Lori F. Cuomo; Dennis P. Santini

[57] ABSTRACT

Epoxidized linear block, random, star-branched block or star-branched random polymers are disclosed which prior to epoxidation contain at least one conjugated diene having at least five carbon atoms of the formula (1)

$$R^1-C=C-C=C-R^6$$
$$\;\;\;\;|\;\;\;|\;\;\;|\;\;\;|$$
$$\;\;\;\;R^2\;R^3\;R^4\;R^5$$

wherein $R^1$–$R^6$ are each hydrogen or a hydrocarbyl group, provided that at least one of $R^1$–$R^6$ is a hydrocarbyl group and the structure of the residual double bond in the polymerized diene of formula (1) has the formula (2)

$$R^I-C=C-R^{III}$$
with $R^{II}$ above and $R^{IV}$ below wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; and the remainder of the conjugated diene different from the diene of formula (1), has at least four carbon atoms of the formula (3)

$$R^7-C=C-C=C-R^{12}$$
$$\;\;\;\;|\;\;\;|\;\;\;\;|\;\;\;\;|$$
$$\;\;\;\;R^8\;R^9\;R^{10}\;R^{11}$$

wherein $R^7$–$R^{12}$ are each hydrogen or a hydrocarbyl group, provided that the structure of the residual double bond in the polymerized diene of formula (3) has the formula (4)

$$R^a-C=C-R^c$$
with $R^b$ above and $R^d$ below wherein $R^a$, $R^b$, $R^c$ and $R^d$ are each hydrogen or a hydrocarbyl group, provided that one of $R^a$ or $R^b$ is hydrogen, one of $R^c$ and $R^d$ is hydrogen.

1 Claim, 2 Drawing Sheets

EPOXIDIZED LIQUID ELASTOMERIC COPOLYMERS

This application is a continuation-in-part of application Ser. No. 08/382,814, filed Feb. 3, 1995 and now U.S. Pat. No. 5,545,783, which is a divisional of Ser. No. 08/179,051, filed Jan. 7, 1994 and now U.S. Pat. No. 5,387,730, which is a divisional of application Ser. No. 07/992,341, filed Dec. 17, 1992 and now U.S. Pat. No. 5,288,937, which is a continuation of application Ser. No. 07/907,959, filed Aug. 6, 1992 and now U.S. Pat. No. 5,210,359 which is a divisional of application Ser. No. 07/466,135, filed Jan. 16, 1990 and now U.S. Pat. No. 5,149,895.

BACKGROUND OF THE INVENTION

1. Field of the Invention

This invention is directed to novel epoxidized liquid block and random copolymers. More particularly, the invention is directed to epoxidized liquid block copolymers wherein epoxide groups are present preponderantly in the terminal blocks.

The invention is also directed to polymers produced by epoxidizing random liquid copolymers having substantially saturated backbones and random, pendant unsaturation which is subsequently converted to epoxide groups.

Crosslinking of the epoxidized polymers of the invention produces elastomeric cured polymers having unusual properties, e.g., high elongation and excellent aging characteristics.

2. Description of Related Art

Elastomers (or rubbers) of either natural or synthetic origin usually require cross-linking, also referred to as curing or vulcanization, for transformation into insoluble, high strength elastomeric products. Before vulcanization, rubbers possess inferior properties and low strength which limit their utility.

There are a number of well known methods for achieving cross-linking of unsaturated elastomers. Such methods include the use of sulfur and accelerators, peroxides, benzoquinone dioxime, certain phenolic resins and similar agents.

Liquid elastomers are well known and are used in various applications. For example, many functionally terminated polybutadiene liquid elastomers are known. These materials are generally highly unsaturated and frequently form the base polymer for polyurethane formulations. The preparation and application of hydroxy-terminated polybutadiene is detailed by J. C. Brosse et al in HYDROXYL-TERMINATED POLYMERS OBTAINED BY FREE RADICAL POLYMERIZATION—SYNTHESIS, CHARACTERIZATION AND APPLICATIONS, ADVANCES IN POLYMER SCIENCE 81, Springer-Verlag, Berlin Heidelberg, 1987, pp 167–220.

Also, liquid polymers possessing acrylate, carboxy- or mercaptoterminals are known. In addition to butadiene, it is known to utilize isoprene as the base monomer for the liquid elastomers. The liquid elastomers may contain additional monomers, such as styrene or acrylonitrile, for controlling compatibility in blends with polar materials, such as epoxy resins.

Also known in the prior art are pure hydrocarbon, non-functionalized liquid rubbers. These liquid elastomers contain varying degrees of unsaturation for utilization in vulcanization. Typical of highly unsaturated liquid elastomers is polybutadiene, e.g., that sold under the name RICON by Ricon Resins, Inc. A liquid polyisoprene which has been hydrogenated to saturate 90% of its original double bonds is marketed as LIR-290 by Kuraray Isoprene Chemical Co. Ltd. Still more highly saturated are liquid butyl rubbers available from Hardman Rubber Co., and Trilene, a liquid ethylene-propylene-diene rubber (EPDM) from Uniroyal Chemical Co. The more highly saturated liquid elastomers exhibit good oxidation and ozone resistant properties. The above prior art liquid elastomers, with either high or low levels of unsaturation, are characterized in that, having random unsaturation, they are randomly crosslinked during vulcanization. The success of vulcanization in incorporating all molecular chains into the final crosslinked network with minimal "loose ends" is termed the degree of network perfection. An imperfect network, wherein crosslinks occur randomly and sometimes not near the end of a molecular chain, produces a vulcanized polymer having poor mechanical and elastomeric properties caused by chain ends which are not a part of the tightly bound network. In order to insure the highest degree of network perfection attainable, randomly unsaturated elastomers must be crosslinked extensively. The large number of crosslinks necessary dictates that the average distance between crosslinks (Mc) must be relatively small in comparison with the dimensions of the whole molecule. Elastomeric properties, such as elongation, depend greatly on Mc—the smaller the Mc the worse are the elastomeric properties, e.g., the lower the elongation of the polymer.

Falk, JOURNAL OF POLYMER SCIENCE: PART A-1, Volume 9, 2617–2623 (1971), the entire contents of which are incorporated herein by reference, discloses a method of selectively hydrogenating 1,4, -polybutadiene in the presence of 1,4-polyisoprene. More particularly, Falk discloses selective hydrogenation of the 1,4-polybutadiene block segment in the block copolymer of 1,4-polybutadiene-1,4-polyisoprene-1,4-polybutadiene and in random copolymers of butadiene and isoprene, with both polymerized monomers having predominantly 1,4-microstructure. Selective hydrogenation is conducted in the presence of hydrogen and a catalyst made by the reaction of organoaluminum or lithium compounds with transition metal salts of 2-ethylhexanoic acid.

Falk, DIE ANGEWANDTE CHEMIE 21 (1972) 17–23 (No. 286), the entire contents of which are also incorporated herein by reference, discloses the selective hydrogenation of 1,4-polybutadiene segments in a block copolymer of 1,4-polybutadiene-1,4-polyisoprene-1,4-polybutadiene.

Hoxmeier, Published European Patent Application 88202449.0, filed on Nov. 2, 1988, Publication Number 0 315 280, published on May 10, 1989, corresponding to U.S. Pat. No. 4,879,349, issued Nov. 7, 1989, discloses a method of selectively hydrogenating a polymer made from at least two different conjugated diolefins. One of the two diolefins is more substituted in the 2,3 and/or 4 carbon atoms than the other diolefin and produces tri- or tetra-substituted double bond after polymerization. The selective hydrogenation is conducted under such conditions as to hydrogenate the ethylenic unsaturation incorporated into the polymer from the lesser substituted conjugated diolefin, while leaving unsaturated at least a portion of the tri- or tetra-substituted unsaturation incorporated into the polymer by the more substituted conjugated diolefin.

Mohajer et al, *Hydrogenated Linear Block Copolymers of Butadiene and Isoprene: Effects of Variation of Composition and Sequence Architecture on Properties*, 23 POLYMER 1523–1535 (September 1982) disclose essentially completely hydrogenated butadiene-isoprene-butadiene (HBIB), HIBI and HBI block copolymers in which butadiene has predominantly 1,4-microstructure.

Kuraray K K, Japanese published patent application Number JP-328 729, filed on Dec. 12, 1987, published on Jul. 4, 1989, discloses a resin composition comprising 70–99% wt. of a polyolefin (preferably polyethylene or polypropylene) and 1–30% wt. of a copolymer obtained by hydrogenation of at least 50% of the unsaturated bonds of isoprene/butadiene copolymer.

U.S. Pat. No. 3,448,174, issued Jun. 3, 1969 to Loveless et al. discloses epoxidized elastomeric copolymers of ethylene, a higher alpha-olefin, e.g., propylene, and a copolymerizable diene, e.g., dicyclopentadiene or 1,4-hexadiene.

Heretofore, the art has failed to produce epoxidized liquid hydrocarbon elastomers having the capability of maintaining relatively large distance between cross-links (high Mc) after curing.

Accordingly, it is an object of this invention to provide epoxidized liquid block polymers capable of being cross-linked to a substantially perfect network with a distance between crosslinks nearly equivalent to the dimensions of the uncross-linked elastomeric molecule. In addition to the expected improvements in elastomeric properties, the unperturbed saturated main chain of the polymers of this invention provides a high degree of oxidative and thermal stability. Unique materials can also be obtained by chemical modification of the epoxidized block polymers of this invention since the epoxy groups of the polymers of the invention can be selectively modified at the terminal ends of the molecules.

It is an additional object of this invention to provide a method for the production of epoxidized random copolymers which, prior to epoxidation, have controlled amounts of unsaturation incorporated randomly in an otherwise saturated backbone. In contrast to EPDM, the level of unsaturation can be inexpensively and easily controlled, e.g., from 1% to 50%, to provide , after epoxidation, a wide variation in curing rate.

SUMMARY OF THE INVENTION

In accordance with this invention there is provided a group of epoxidized liquid copolymers each of which before epoxidation is a copolymer of at least one hydrocarbon conjugated diene (I) monomer containing at least five (5) carbon atoms, with at least one carbon atom of each pair of residual double-bonded carbon atoms of polymerized conjugated diene (I) units being additionally single-bonded to two carbon atoms, and at least one hydrocarbon conjugated diene (B), which is different from conjugated diene (i) and contains at least four (4) carbon atoms, with each residual double-bonded carbon atom of polymerized conjugated diene (B) units being additionally bonded to a hydrogen atom.

The copolymer prior to epoxidation may be for example, a block copolymer wherein the terminal blocks are each a polymer of and I diene (I polymer) or a copolymer of at least one I diene and an aryl-substituted olefin, and at least one interior block in each polymer chain is a polymer of a B diene (B polymer). Thus, the copolymer may comprise at least three alternating blocks:

$$(I)_x\text{-}(B)_y\text{-}(I)_x$$

wherein I is a block of at least one polymerized conjugated diene having at least five (5) carbon atoms and the following formula

wherein $R^1$–$R^6$ are each hydrogen or a hydrocarbyl group, provided that at least one of R1–R6 is a hydrocarbyl group and further provided that the structure of the residual double bond in the polymerized block I has the following formula

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; B is a block of a polymer of at least one conjugated diene, different from that used to polymerize the I block, having at least four (4) carbon atoms and the following formula

wherein $R^7$–$R^{12}$ are each hydrogen or a hydrocarbyl group, provided that the structure of the residual double bond in the polymerized conjugated diene of formula (3) (block B) has the following formula:

wherein $R^a$, $R^b$, $R_c$ and $R^d$ are each hydrogen (H) or a hydrocarbyl group, provided that one of $R^a$ or $R^b$ is hydrogen, one of $R^c$ or $R^d$ is hydrogen and at least one of $R^a$, $R^b$, $R^c$ or $R^d$ is a hydrocarbyl group; x is at least 1, preferably 1 to 30, more preferably 2 to 20, and most preferably 3 to 10, and y is at least 25, preferably 30 to 275, more preferably 85 to 225, and most preferably 130 to 200. It will be apparent to those skilled in the art that in the residual double bond of formula (2), $R^I$, $R^{II}$, $R^{III}$ and $R^{IV}$ may all be hydrocarbyl groups.

The hydrocarbyl group or groups in the formulae (1) and (2) are the same or different and they are substituted or unsubstituted alkyl, alkenyl, cycloalkyl, cycloalkenyl, aryl, alkaryl or aralkyl groups or any isomers thereof. Examples of suitable conjugated dienes used to polymerize the I block are isoprene, 2,3-dimethyl butadiene, 2-methyl-1,4-pentadiene or myrcene. The hydrocarbyl groups in formulae (3) and (4) are the same as those described above in conjunction with the discussion of formulae (1) and 2. Suitable conjugated dienes used to polymerize the B block are 1,3-butadiene or 1,3-pentadiene. After the polymerization is completed, the block polymer may be hydrogenated so that the block B is selectively hydrogenated to such an extent that it contains substantially none of the original unsaturation, while each of the blocks I retains a sufficient amount of its original unsaturation for conversion to the requisite epoxy groups in the terminal I blocks. Alternatively, the polymer may be epoxidized prior to selective hydrogenation of the B blocks, in which case all or most of the epoxidation occurs in the terminal I blocks, with little or no epoxidation occurring in the B blocks. The oxidative and thermal stability of the epoxidized polymer may then be improved by hydrogenation to eliminate the ethylenic unsaturation in the B blocks.

In another embodiment, the polymer prior to epoxidation may be a block copolymer comprising at least three alternating blocks:

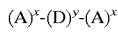

wherein the block A is a block or random copolymer of about 30 to about 70%, preferably about 40 to about 60%, by mole of at least one aryl-substituted olefin, such as styrene, 2-phenyl alpha-olefins, alkylated styrene, vinyl naphthalene or alkylated vinyl naphthalene, and about 30 to about 70%, preferably about 40 to about 60%, by mole of at least one conjugated diene of formula (1), discussed above; D is a block of a polymer of at least one conjugated diene of formula (3), discussed above, which is different from the conjugated diene of formula (1) used to polymerize the block (A); x is about 2 to about 30%, preferably about 4 to about 16%, by wt., of the weight of the triblock copolymer, and y is about 40 to about 96%, preferably about 68 to about 92%, by wt., of the weight of the triblock copolymer. Examples of suitable conjugated dienes used to polymerize the A block are isoprene, 2,3-dimethyl butadiene, myrcene or 2-methyl-1,3-pentadiene. Suitable conjugated dienes used to polymerize the D block are 1,3-butadiene or 1,3-pentadiene.

After this block copolymer is polymerized, it may be hydrogenated, so that the block D is selectively hydrogenated to such an extent that it contains substantially none of the original unsaturation, while each of the blocks A retains a sufficient amount of the original unsaturation of the conjugated diene present in each of the terminal A blocks for conversion to epoxy groups. As is the case with the I-B-I polymers, the A-D-A polymers may also be epoxidized prior to selective hydrogenation, with all or most of the epoxidation occurring in the terminal A blocks and little or no epoxidation occurring in the D blocks, and with hydrogenation to eliminate all or most of the unsaturation in the D blocks being carried out subsequent to epoxidation. The block copolymer of this embodiment is terminated at both ends with a block A.

The blocks A and I are referred to hereinafter as the "terminal" blocks, and the blocks B and D as the "central" or "middle" blocks. Yet another embodiment is directed to an epoxidized block copolymer which prior to epoxidation comprises at least three alternating blocks:

wherein the blocks I, D and A are polymerized from the same monomers as discussed above for the respective blocks. The block copolymer comprises about 1 to about 15, preferably about 2 to about 8% wt. of the block I, about 2 to about 30, preferably about 4 to about 16% wt. of the blocks A and about 55 to about 97, preferably about 76 to about 94% wt. of the blocks D. The block A of this copolymer is either a block or a random copolymer of about 30 to about 70% by mole of at least one aryl-substituted olefin and about 30 to about 70% by mole of at least one conjugated diene of formula (1). As is the case with the previously discussed block polymers, the I-D-A polymers may also be selectively hydrogenated prior or subsequent to epoxidation, with all or most of the epoxidation occurring in the terminal I or A blocks and little or no epoxidation in the D blocks if epoxidation is carried out prior to hydrogenation.

Another embodiment of the invention is directed to epoxidized random copolymers of at least one conjugated diene of formula (1) and at least one conjugated diene of formula (3), both discussed above, provided that the diene of formula (3) is different from the diene of formula (1). This random copolymer contains about 1.0 to about 25, preferably about 1.0 to about 10% by mole of the polymerized conjugated diene of formula (1) and about 75 to about 99%, preferably about 90 to about 99% by mole of the conjugated diene of formula (3). This random copolymer may also be selectively hydrogenated, so that the polymerized diene of formula (3) contains substantially none of the original unsaturation, while the polymerized diene of formula (1) retains a sufficient amount of the original unsaturation for conversion to the desired epoxy groups, or the random copolymer may be epoxidized prior to hydrogenation in which case the polymerized units of the diene of formula (1) tend to be epoxidized to a much greater degree than the polymerized units of the diene of formula (3), after which the copolymer may be hydrogenated to eliminate the unsaturation in the polymerized units of the diene of formula (3).

Another embodiment of this invention is directed to epoxidized random copolymers of at least one aryl-substituted olefin, at least one conjugated diene of formula (1) and at least one conjugated diene of formula (3), both discussed above, provided that the conjugated diene of formula (1) is different from the conjugated diene of formula (3). This random copolymer prior to epoxidation contains about 0.3 to about 15% by mole of the aryl-substituted olefin, about 1.0 to about 25%, preferably about 1.0 to about 10%, by mole of the conjugated diene of formula (1), and the remainder of the conjugated diene of formula (3). This random copolymer is also hydrogenated, so that the polymerized diene of formula (3) is selectively hydrogenated to such an extent that it contains essentially none of the original unsaturation, while the polymerized diene of formula (1) retains a sufficient amount of the original unsaturation for conversion to the requisite epoxy groups, or the random copolymer may be epoxidized prior to selective hydrogenation as described in the previous paragraph in connection with random copolymers not necessarily containing polymerized aryl-substituted olefin units.

Yet another embodiment of the invention is directed to epoxidized star-branched block and random polymers. The star-branched block polymers prior to epoxidation are composed of any combination of blocks I and B, A and D, or I, D and A, providing that each free end (i.e., uncoupled end) of the star-branched polymer is either an I or an A block, respectively. The star-branched block polymers may be selectively hydrogenated to such an extent that blocks B or D contain substantially none of the original unsaturation, while each of the blocks I or A, respectively, retains a sufficient amount of the original unsaturation of the conjugated dienes present for conversion to epoxy groups or the epoxidation of the star-branched polymer may be carried out first followed by selective hydrogenation as described previously for straight chain block copolymers.

The star-branched random polymers are made prior to epoxidation, from any combination of dienes of formulae (1) and (3), providing that the diene of formula (1) is different from the diene of formula (3), or from at least one aryl-substituted olefin, at least one diene of formula (1) and at least one diene of formula (3), providing that the diene of formula (3) is different from the diene of formula (1). The star-branched random polymers may be selectively hydrogenated, so that the polymerized diene of formula (3) contains none of the original unsaturation, while the polymerized diene of formula (1) retains a sufficient amount of the original unsaturation for conversion to epoxy groups, or the polymer may be epoxidized before hydrogenation as described previously for straight chain random copolymers.

The copolymers to be epoxidized of all embodiments are prepared under anionic polymerization conditions. After the selective hydrogenation reaction, the hydrogenation catalyst is removed from the polymer.

In all embodiments of this invention, whenever a reference is made to the "residual double bond" of the block or random polymer (or copolymer), it is understood to be the residual double bond prior to the hydrogenation or epoxidation reaction. The structure of the residual double bond can be determined in any conventional manner, as is known to those skilled in the art, e.g., by infrared (IR) or NMR analysis.

The term "original unsaturation", as used herein, means the sum total of the unsaturated groups present in all blocks of the copolymer prior to the selective hydrogenation or epoxidation reaction. The unsaturation can be quantified in any conventional manner, e.g., by reference to the Iodine Number of the polymer. For example, for a block copolymer of the first embodiment wherein the I blocks are polyisoprene and the B block is polybutadiene, the Iodine Number before selective hydrogenation or epoxidation for each of the I blocks is 373 and for the B block it is 470. After selective hydrogenation is completed and before epoxidation, when the sequence of reactions is hydrogenation followed by epoxidation, the Iodine Number for each of the I blocks is about 75 to about 373, and for the B blocks it is about 0 to about 50, preferably about 0 to about 2.5 and most preferably about 0 to about 1.

In any polymers of any of the embodiments of the block copolymers which may be used to prepare the epoxidized copolymers of this invention, the microstructure of the polymerized conjugated diene of formula (3), e.g., blocks B or D in the block copolymers, must be such that the polymer is not excessively crystalline after the selective hydrogenation reaction, i.e., after the selective hydrogenation reaction the polymer must retain its elastomeric properties e.g., the polymer should contain not more than about 10% of polyethylene crystallinity. This is accomplished by introducing side branches into the polymerized conjugated diene of formula (3), e.g., by controlling the microstructure of 1,3-butadiene if it is the predominant monomer in the diene of formula (3), by using a mixture of dienes of formula (3) containing less than predominant amounts of 1,3-butadiene or by using a single diene of formula (3), other than 1,3-butadiene. More particularly, if the conjugated diene(s) of formula (3) is predominantly (at least 50% by mole) 1,3-butadiene, the side branches are introduced into the polymer by insuring that the polymerized diene of formula (3) contains a sufficient amount of the 1,2-units to prevent the selectively hydrogenated polymer from being excessively crystalline. Thus, if the conjugated diene of formula (3) is predominantly (at least 50% by mole, e.g., 100% by mole) 1,3-butadiene, the polymerized diene of formula (3), prior to the selective hydrogenation reaction, must contain not more than about 75% wt., preferably about 10 to about 70% wt., and most preferably about 35 to about 55% wt. of the 1,4-units, and at least about 25% wt., preferably about 30 to about 90% wt., and most preferably about 45 to about 65% wt. of the 1,2-units. If the polymerized diene(s) of formula (3) contains less than 50% by mole of 1,3-butadiene, e.g., 1,3-pentadiene is used as the only diene of formula (3), the microstructure of the polymerized diene of formula (3) prior to the selective hydrogenation reaction is not critical since, after hydrogenation, the resulting polymer will contain substantially no crystallinity.

In all embodiments of the invention, mixtures of dienes of formulae (1) or (3) may be used to prepare block copolymers (I)x-(B)y-(I)x, (A)x-(D)y-(A)x or I-D-A, any of the random copolymers or star-branched block and random polymers which may be used to prepare the epoxidized polymers of the invention. Similarly, mixtures of aryl-substituted olefins may also be used to prepare block, random or star-branched copolymers which are epoxidized in accordance with this invention. Accordingly, whenever a reference is made herein to a diene of formulae (1) or (3), or to an aryl-substituted olefin, it may encompass more than one diene of formulae (1) or (3), respectively, and more than one aryl-substituted olefin.

DETAILED DESCRIPTION OF THE INVENTION

Figure 1:
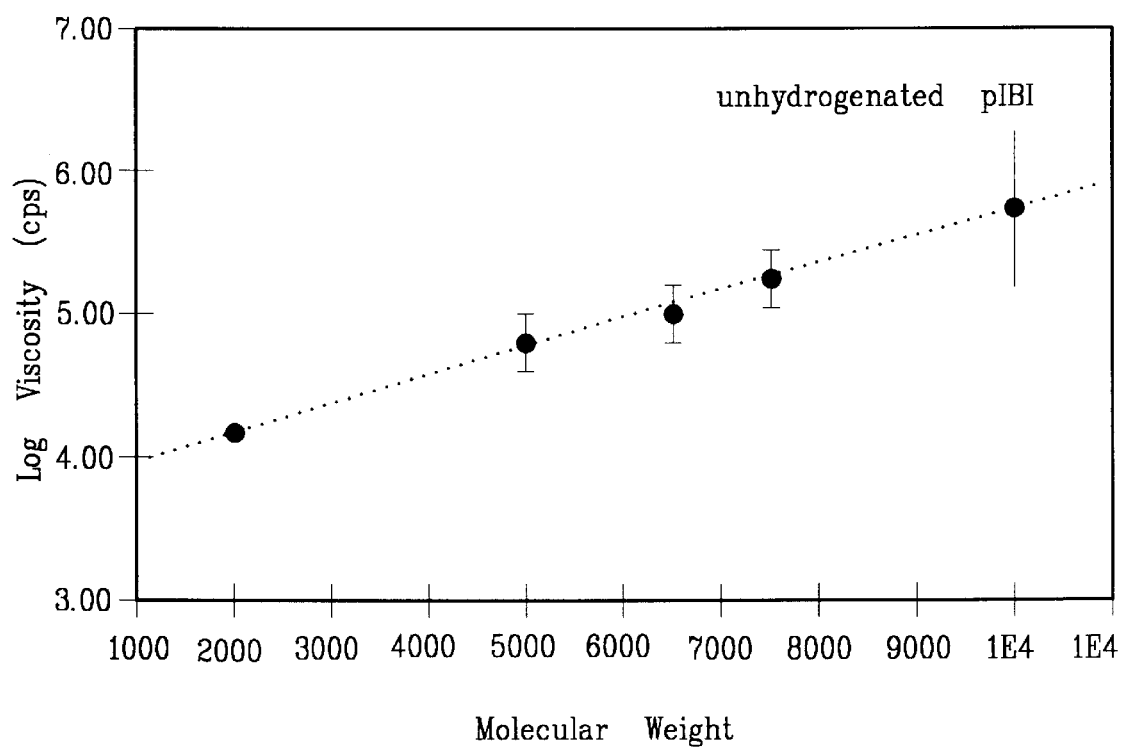
FIG. 1 shows the relationship of viscosity as a function of molecular weight for the unhydrogenated and unepoxidized isoprene-butadiene-isoprene triblock polymer of this invention.

The epoxidized block copolymers of this invention may be linear or straight chain polymers comprising three or more alternating blocks, identified above. Linear block copolymers having more than three blocks are contemplated herein, although they do not appear to exhibit better properties than the block copolymers containing only three blocks. However, star-branched block polymers containing any combination and number of blocks I and B, A and D, or I, D and A are also contemplated herein, providing that they are terminated either by blocks I or A, respectively. The central (middle) block of each linear three block unit is substantially completely saturated, while the terminal blocks if not previously epoxidized contain controlled levels of unsaturation providing a hydrocarbon elastomer with α-ω unsaturation which is subsequently converted to epoxy groups. When the polymers are cross-linked through epoxy groups, the length of the central saturated block defines the distance between crosslinks (Mc) in the cured elastomers. Because of the α-ω placement of the unsaturation prior to epoxidation, very low levels of residual double bonds converted to epoxy groups are required to attain excellent cross-linking. The low level of unsaturation in the selectively hydrogenated and epoxidized triblock polymer provides excellent oxidative stability to the polymers of this invention.

Without wishing to be bound by any theory, it is believed that the α-ω placement of unsaturation in the polymers of this invention prior to epoxidation and curing, imparts to the polymers excellent elastomeric properties absent in prior art thermosetting liquid elastomers which require a multiplicity of relatively closely spaced crosslinks.

The combination of elastomeric properties and oxidative stability possessed by the polymers of this invention makes them suitable for many end uses, such as sealants, caulks and adhesives.

Many variations in composition, molecular weight, molecular weight distribution, relative block lengths, microstructure, branching and $T_g$ (glass transition temperature) attainable with the use of anionic techniques employed in the preparation of our polymers will be obvious to those skilled in the art.

While not wishing to limit the molecular weight range of epoxidized liquid elastomers prepared according to our invention, the minimum molecular weight for these liquid polymers is at least about 2,000, preferably about 5,000 to about 15,000, and most preferably about 7,500 to about 10,000. Star-branched block and random polymers of this invention may have substantially higher molecular weights and still retain liquid properties. For example, epoxidized liquid star-branched block polymers having molecular weight of about 34,000 have been prepared. The block copolymers of this invention are curable. Without wishing to be bound by any theory of operability, it is believed that they can be crosslinked in a controlled manner through the unsaturated groups on the terminal blocks to provide a very strong and orderly matrix of crosslinkages having almost uniform distribution of molecular weights between crosslinks, Mc. The epoxidized random and star-branched copolymers of this invention are also curable. The designation Mc, as used herein for the block copolymers means the length of the middle block. For random copolymers, Mc is calculated by dividing number average molecular weight, Mn, of the polymer by the average number of crosslinks per chain plus 1.

The invention will be described hereinafter in terms of the embodiments thereof summarized above. However, it will be apparent to those skilled in the art, that the invention is not limited to these particular embodiments, but, rather, it covers all the embodiments encompassed by the broadest scope of the description of the invention.

Epoxidized Liquid Block Copolymers From at Least Two Dissimilar Conjugated Dienes In this embodiment of the invention, the polymer prior to epoxidation is a block copolymer comprising at least three alternating blocks:

$$(I)_x\text{-}(B)_y\text{-}(I)_x$$

wherein:

I is a block of at least one polymerized conjugated diene having at least five (5) carbon atoms and the following formula

$$R^1\text{—}C\text{=}C\text{—}C\text{=}C\text{—}R^6 \quad (1)$$
$$\phantom{R^1\text{—}}| \phantom{\text{=}C}| \phantom{\text{—}C}| \phantom{\text{=}C}|$$
$$\phantom{R^1\text{—}C\text{=}}R^2 \phantom{C\text{—}} R^3 \phantom{C\text{=}} R^4 \phantom{C\text{—}} R^5$$

wherein $R^1$–$R^6$ are each hydrogen or a hydrocarbyl group, provided that at least one of $R^1$–$R^6$ is a hydrocarbyl group, and further provided that the structure of the residual double bond in the polymerized block I has the following formula:

$$R^{III} \qquad\qquad\qquad (2)$$
$$|$$
$$R^I\text{—}C\text{=}C\text{—}R^{III}$$
$$|$$
$$R^{IV}$$

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups;

B is a block of at least one polymerized conjugated diene, different from that used to polymerize block I, having at least four (4) carbon atoms and the following formula:

$$R^7\text{—}C\text{=}C\text{—}C\text{=}C\text{—}R^{12} \quad (3)$$
$$\phantom{R^7\text{—}}| \phantom{\text{=}C}| \phantom{\text{—}C}| \phantom{\text{=}C}|$$
$$\phantom{R^7\text{—}C\text{=}}R^8 \phantom{C\text{—}} R^9 \phantom{C\text{=}} R^{10} \phantom{C\text{—}} R^{11}$$

wherein $R_7$–$R^{12}$ are each hydrogen or a hydrocarbyl group, provided that the structure of the residual double bond in the polymerized block B has the following formula:

$$R^b \qquad\qquad\qquad (4)$$
$$|$$
$$R^a\text{—}C\text{=}C\text{—}R^c$$
$$|$$
$$R^d$$

wherein $R^a$, $R^b$, $R^c$ and $R^d$ are each hydrogen (H) or a hydrocarbyl group, provided that one of $R^a$ or $R^b$ is hydrogen, one of $R^c$ or $R^d$ is hydrogen and at least one of $R^a$, $R^b$, $R^c$ or $R^d$ is a hydrocarbyl group;

x is at least 1, preferably 1 to 15, more preferably 2 to 10, and most preferably 2 to 7, y is at least 25, preferably 90 to 300, more preferably 130 to 200, and most preferably 140 to 200. The above definition of x means that each of the I blocks is polymerized from at least 1, preferably from 1–15, more preferably from 2–10 and most preferably from 2–7 monomer units. For some special applications, each of the I blocks is polymerized from 20–30 monomer units.

Similarly, the above definition of y means that each of the B blocks is polymerized from at least 25, preferably from 90 to 300, more preferably from 130 to 200, and most preferably from 140 to 200 monomer units. In the residual double bond of formula (2), $R^I$, $R^{II}$, $R^{III}$ and $R^{IV}$ may all be hydrocarbyl groups.

The structures of the residual double bonds defined by formulae (2) and (4) are necessary to produce copolymers which can be selectively hydrogenated and epoxidized in the manner described herein, to produce the selectively hydrogenated and epoxidized block and random copolymers of this invention.

The block copolymer prior to epoxation comprises about 0.5 to about 25%, preferably about 1 to about 5% by wt. of the I blocks, and about 75 to about 99.5%, preferably about 95 to about 99% by wt. of the B blocks.

The hydrocarbyl group or groups in the formulae (1) and (2) are the same or different and they are substituted or unsubstituted alkyl, alkenyl, cycloalkyl, cycloalkenyl, aryl, alkaryl or aralkyl groups or any isomers thereof. Suitable hydrocarbyl groups are alkyls of 1–20 carbon atoms, alkenyls of 2–20 carbon atoms, cycloalkyls of 5–20 carbon atoms, cycloalkenyls of 5–20 carbon atoms, aryls of 6–12 carbon atoms, alkaryls of 7–20 carbon atoms or aralkyls of 7–20 carbon atoms. Examples of suitable alkyl groups are methyl, ethyl, propyl, butyl, pentyl, hexyl, heptyl, octyl, decyl, methyl-decyl or dimethyl-decyl. Examples of suitable alkenyl groups are ethenyl, propenyl, butenyl, pentenyl or hexenyl. Examples of suitable cycloalkyl groups are cyclohexyl or methylcyclohexyl. Examples of suitable cycloalkenyl groups are 1-, 2-, or 3-cyclohexenyl or 4-methyl-2-cyclohexenyl. Examples of suitable aryl groups are phenyl or diphenyl. Examples of suitable alkaryl groups are 4-methyl-phenyl (p-tolyl) or p-ethyl-phenyl. Examples of suitable aralkyl groups are benzyl or phenethyl. Suitable conjugated dienes of formula (1) used to polymerize the I block are isoprene, 2,3-dimethyl-butadiene, 2-methyl-1,3-pentadiene, myrcene, 3-methyl-1,3-pentadiene, 4-methyl-1,3-pentadiene, 2-phenyl-1,3-butadiene, 2-phenyl-1,3-pentadiene, 3-phenyl-1,3-pentadiene, 2,3-dimethyl-1,3-pentadiene, 2-hexyl-1,3-butadiene, 3-methyl-1,3-hexadiene, 2-benzyl-1,3-butadiene, 2-p-tolyl- 1,3-butadiene or mixtures thereof, preferably isoprene, myrcene or 2-methyl-1,3-pentadiene, and most preferably isoprene.

The hydrocarbyl group or groups in the formula (3) may or may not be the same as those in formula (4). These hydrocarbyl groups are the same as those described above in conjunction with the discussion of the hydrocarbyl groups of formulae (1) and (2). Suitable monomers for the B block are 1,3-butadiene, 1,3-pentadiene, 2,4-hexadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene or mixtures thereof, preferably 1,3-butadiene, 1,3-pentadiene, 2,4-hexadiene or 1,3-hexadiene, and most preferably it is 1,3-butadiene. It is preferred that each of the B blocks is polymerized from a single monomer.

The block copolymer of this embodiment is terminated at both ends with a block I.

The scope of this embodiment, and of any other embodiments of the invention wherein the block B is used, also encompasses polymers wherein the central block B may comprise copolymers of one or more conjugated diene of formula (3) and controlled amounts (about 0.3 to about 30 mole %) of an aryl-substituted olefin, e.g., styrene or other suitable monomers (such as alkylated styrene, vinyl napthalene or alkylated vinyl naphthalene) incorporated for control of glass transition temperature ($T_g$), density, solubility parameters and refractive index. Suitable aryl-substituted olefins are those described below in conjunction with the second embodiment of the invention. Similarly, the scope of this embodiment also encompasses polymers wherein the central block B may be comprised of copolymers of one or more conjugated diene of formula (3) and any other anionically polymerizable monomer capable of polymerizing with the conjugated diene of formula (3).

It will be apparent to those skilled in the art that proper choice of polymerization parameters can produce polymers to be subjected to epoxidation with a great variety of compositional and structural differences, falling within the scope of our invention. Changes in composition of the central block B control the nature of the rubbery properties.

The block copolymer to be subjected to epoxidation is polymerized by any conventional block copolymerization process, such as anionic polymerization, discussed in detail below. As will be apparent to those skilled in the art, the copolymer of this embodiment contains at least three alternating blocks, I-B-I, referred to herein as the triblocks or triblock units, but it may contain an unlimited number of blocks, so long as the entire block copolymer is terminated at both ends by the I blocks. Polymers having more than three blocks (such as five) allow crosslinking to take place at the ends and in the central portion, but maintain a controlled large distance between crosslinks. It is important to have the block copolymer terminated at each end with the I blocks to assure that there are unsaturated groups at each end of the block copolymer enabling the block copolymer to be epoxidized at the terminal ends thereof.

After the block copolymer is polymerized and before or after epoxidation, it may be subjected to a selective hydrogenation reaction during which the B blocks of the block copolymer are selectively hydrogenated to such an extent that they contain substantially none of the original unsaturation, while the I blocks, if not already epoxidized, retain a sufficient amount of their original unsaturation for conversion to epoxy groups. Generally, for a block copolymer wherein the I and B blocks are polymerized from any of the monomers discussed above, the Iodine Number for the I blocks after the selective hydrogenation reaction but before epoxidation is about 20 to about 100%, preferably about 50 to about 100% of the Iodine Number prior to the selective hydrogenation and epoxidation reactions and for the B blocks it is about 0 to about 10%, preferably about 0 to about 0.5%, and most preferably about 0 to about 0.2% of the Iodine Number prior to selective hydrogenation. The Iodine Number, as is known to those skilled in the art, is defined as the theoretical number of grams of iodine which will add to the unsaturation in 100 grams of olefin and is a quantitative measure of unsaturation.

In this embodiment of the invention, although the microstructure of the I blocks is not critical and may consist of 1,2-, 3,4- and/or 1,4-units, schematically represented below for the polyisoprene blocks, when a polar compound is used during the polymerization of the I block, the I blocks comprise primarily (at least about 80% wt.) 3,4-units, the rest being primarily (about 20% wt.) 1,2-units; when the polar compound is not used during the polymerization of the I block, the I blocks comprise primarily (about 80% wt.) 1,4-units, the rest being primarily 1,2- and 3,4- units.

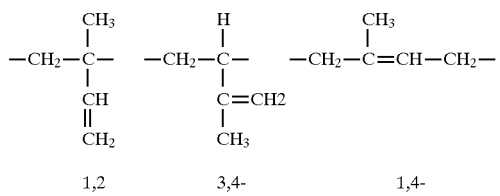

The microstructure of the B blocks, when the predominant monomer used to polymerize the B blocks is 1,3-butadiene, should be a mixture of 1,4 and 1,2- units schematically shown below for the polybutadiene blocks:

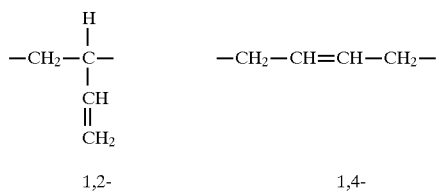

since the hydrogenation of the predominantly 1,4-microstructures produces a crystalline polyethylene segment. The microstructure of the I and B blocks (as well as of the polymerized conjugated dienes of formulae (1) or (3) in any polymers of this invention) is controlled in a conventional manner, e.g., by controlling the amount and nature of the polar compounds used during the polymerization reaction, and the reaction temperature. In one particularly preferred embodiment, the B block contains about 50% of the 1, 2- and about 50% of the 1,4-microstructure. If the B block is poly-1,3-butadiene, the hydrogenation of the B segment containing about 50 to about 60% of the 1,2-microstructure content produces an elastomeric center block which is substantially an ethylene-butene-1 copolymer having substantially no crystallinity. If the B block is polymerized from 1,3-pentadiene, it is preferred that it have predominantly (at least 50%) of 1,4-microstructure which, after hydrogenation, produces a substantially non-crystalline elastomeric block.

The terms 1,2-, 1,4-, and 3,4-microstructure or units as used in this application refer to the products of polymerization obtained by the 1,2-, 1,4- and 3,4-, respectively, additions of two monomer units.

We surprisingly discovered that the polymerized conjugated dienes of formula (3), e.g., the B blocks, of the polymers of this invention are selectively hydrogenated in our hydrogenation process prior to epoxidation much faster than the polymerized conjugated dienes of formula (1), e.g., the I blocks. This is not evident from the teachings of Falk, discussed above, because Falk teaches that double bonds of the disubstituted 1,4-polybutadiene units are hydrogenated selectively in the presence of double bonds of the trisubstituted 1,4-polyisoprene units (which are not hydrogenated). We surprisingly discovered that the disubstituted double bonds of the 1,4-polybutadiene units are hydrogenated along with the monosubstituted double bonds of the 1,2-polybutadiene units, while the disubstituted double bonds of the 3,4-polyisoprene units are hydrogenated at a much slower rate than the aforementioned polybutadienes. Thus, in view of Falk's disclosure it is surprising that the disubstituted double bonds of the 1,4-polybutadiene units are hydrogenated selectively in the presence of the disubstituted double bonds of the 3,4-polyisoprene units. This is also surprising in view of the teachings of Hoxmeier, Published European Patent Application, Publication No. 0 315 280, who discloses that the disubstituted double bonds of the 1,4-polybutadiene units, monosubstituted double bonds of the 1,2-polybutadiene units and disubstituted double bonds of the 3,4-polyisoprene units are hydrogenated simultaneously at substantially the same rates. For example, for the block copolymers of this invention, wherein the I block is polyisoprene and the B block is polybutadiene, Fourier Transform Infrared (FTIR) analysis of selectively hydrogenated triblock polymers indicates that the hydrogenation of the double bonds of the 1,2-polybutadiene units proceeds most rapidly, followed by the hydrogenation of the double bonds of the 1,4-polybutadiene units. Infrared absorptions caused by these groups disappear prior to appreciable hydrogenation of the polyisoprene units.

After the I-B-I block copolymer is prepared, it is subjected to a selective hydrogenation reaction before or after epoxidation to hydrogenate primarily the B block of each of the triblocks. The selective hydrogenation reaction and the catalyst are described in detail below. After the hydrogenation reaction is completed, the selective hydrogenation catalyst is removed from the block copolymer, and the polymer is isolated by conventional procedures, e.g., alcohol flocculation, steam stripping of solvent or non-aqueous solvent evaporation. An antioxidant, e.g., Irganox 1076 (from Ciba-Geigy), is normally added to the polymer solution prior to polymer isolation.

Epoxidized Triblock Copolymer Of Poly-Diene Center Block And Terminal Blocks of Aryl-Substituted Olefin/Diene Copolymer In this alternative embodiment of the invention, the block copolymer prior to epoxidation comprises at least one triblock of:

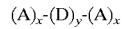

wherein the block A is a copolymer of about 30 to about 70%, preferably about 40 to about 60% by mole of at least one aryl-substituted olefin, and about 30 to about 70%, preferably about 40 to about 60%, by mole of at least one conjugated diene of formula (1), defined above. The block A is either a block or a random copolymer. The most preferred conjugated diene of formula (1) is isoprene. In this block copolymer, D is a block of a polymer of at least one conjugated diene of formula (3), discussed above, which is different from the conjugated diene of formula (1) used to polymerize the block A. In this block copolymer, x represents the total number of monomer units in the block A, such that the block copolymer comprises about 2 to about 30%, preferably about 4 to about 16% by wt. of the A blocks and y represents the total number of monomer units in the block D, such that the block copolymer comprises about 40 to about 96%, preferably about 68 to about 92% by wt. of the D blocks. The block copolymer of this embodiment may contain several blocks of the aforementioned formula, e.g., 5, so long as it is terminated at both ends with the block A, but, preferably, it contains only three blocks A-D-A. Suitable aryl-substituted olefins used to polymerize the block A have the formula:

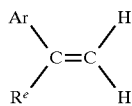

where Ar is phenyl, alkyl-substituted phenyl, naphthyl or alkyl-substituted naphthyl, and $R^e$ is hydrogen, methyl, ethyl, propyl, butyl or aryl. Examples of suitable aryl-substituted olefins are styrene, 2-phenyl alpha-olefins, such as alpha-methyl styrene, 1,1-diphenyl ethylene, alkylated styrenes, vinyl naphthalene, or any alkylated vinyl naphthalenes. Suitable alkyl substituents in the alkylated styrenes or alkylated vinyl naphthalenes are methyl, ethyl, propyl, sec-butyl and tert-butyl. Each of the alkylated styrenes or vinyl naphthalenes may contain one or more alkyl substituents. Preferred aryl-substituted olefins are styrene, vinylnaphthalene, alpha-methyl styrene, vinyltoluene and diphenylethylene. The microstructure of the polymerized diene of formula (1) is not critical, but can be controlled in the manner discussed above. The block copolymer of this embodiment is polymerized by any conventional block copolymerization process, such as anionic polymerization discussed in detail below.

The scope of this embodiment, and of any other embodiment of the invention wherein the block D is used, also encompasses polymers wherein the central (middle) block D may be comprised of copolymers of one or more conjugated diene of formula (3) and controlled amounts (about 0.3 to about 30 mole %) of an aryl-substituted olefin, e.g., styrene or other suitable monomers (such as alkylated styrene, vinyl napthalene or alkylated vinyl napthalene), incorporated for control of glass transition temperature ($T_g$), density, solubility parameters and refractive index.

The scope of this embodiment, and of any other embodiment of the invention using the block A, also encompasses polymers wherein the blocks A are prepared by, initially, polymerizing at least one aryl-substituted olefin alone, and subsequently reacting the resulting poly-aryl-substituted olefin with any compounds which, after chemical reaction with the poly-aryl-substituted olefin, will provide the residual double bonds on the A blocks, as defined above in conjunction with the discussion of the conjugated diene of formula (1). The resulting block A will therefore have substantially the same residual unsaturation (residual double bonds) on the terminal blocks A as any other block A made in accordance with this embodiment (or any other embodiment using the block A).

In the most preferred embodiment, the block A of this triblock copolymer is polymerized from isoprene and styrene in the molar proportion of about 1:1. Most preferably, in this embodiment of the invention, the A block is polymerized from isoprene and styrene, and the D block from 1,3-butadiene, in such proportions that the final copolymer comprises about 1.5 to about 6% wt. of the isoprene, about 2.5 to about 10% wt. of the styrene, and about 84 to about 96% wt. of the butadiene units.

After the polymerization is completed, the block copolymer may be subjected to a selective hydrogenation reaction before or after epoxidation. After selective hydrogenation, the polymer, if not previously epoxidized, contains a sufficient amount of its original unsaturation in the terminal blocks A to form the requisite number of epoxy groups, thereby permitting chemical crosslinking in the manner discussed below, while the middle block D contains substantially none of the original unsaturation. For example, for a block copolymer wherein the A blocks are copolymers of styrene and isoprene and the D block is polybutadiene, the Iodine Number before selective hydrogenation and epoxidation for each of the A blocks is 120–180 and for the D block it is 470. After selective hydrogenation but before epoxidation, the Iodine Number for each of the A blocks is about 20 to about 180 and for the D block it is about 0 to about 10, and preferably about 0 to about 2.5. Generally, for a block copolymer wherein the A and D blocks are polymerized from any of the monomers suitable for their polymerization, discussed above, the Iodine Number for the A blocks after the selective hydrogenation but before epoxidation is completed is about 20 to about 100%, preferably about 50 to 100% of the Iodine Number prior to the selective hydrogenation and epoxidation reactions, and for the D blocks it is about 0 to about 10%, preferably about 0 to about 0.5% of the Iodine Number prior to the selective hydrogenation reaction. Thus, in this embodiment, the block D is also selectively hydrogenated in the same manner as discussed above for the central block B of the first embodiment of the invention.

The block copolymer of this embodiment is also a liquid, and, after or before selective hydrogenation, the unsaturated groups in the terminal A blocks of each of the triblocks provide a means of epoxidizing the copolymer in the manner discussed elsewhere in this application.

Epoxidized Triblock Copolymer of at Least One Poly-Diene Center Block, and at Least One Terminal Block of Aryl-Substituted Olefin/Diene Copolymer In this embodiment of the invention, the block copolymer prior to epoxidation comprises at least one triblock of:

I-D-A where the block I is a polymer of at least one polymerized diene of formula (1), defined above, the block D is a polymer of at least one conjugated diene of formula (3), defined above, which is different from the conjugated diene of formula (1), and the block A is a copolymer of at least one aryl-substituted olefin and at least one conjugated diene of formula (1), both defined above. The block A is a copolymer of about 30 to about 70%, preferably about 40 to about 60% by mole of at least one aryl-substituted olefin, and about 30 to about 70%, preferably about 40 to about 60% by mole of at least one conjugated diene of formula (1), preferably isoprene. This block copolymer comprises about 1 to about 15, preferably about 2 to about 8% wt. of the blocks I, about 2 to about 30, preferably about 4 to about 16% wt. of the blocks A, and about 55 to about 97, preferably about 76 to about 94% wt. of the blocks D. The block of this embodiment may also contain several, e.g. 5–7, blocks of the aforementioned formulae so long as it is terminated at both ends thereof with blocks I or A. The block copolymer is polymerized by any conventional block copolymerization process, such as anionic polymerization, discussed in detail below.

The scope of this embodiment of the invention also encompasses polymers to be epoxidized wherein the central block D may be comprised of copolymers of one or more conjugated diene of formula (3) and controlled amounts (about 0.3 to about 30 mole %) of an aryl-substituted olefin, e.g., styrene or other suitable monomers (such as alkylated styrene, vinyl napthalene or alkylated vinyl napthalene), incorporated for control of glass transition temperature ($T_g$), density, solubility parameters and refractive index. Suitable aryl-substituted olefins are those described below in conjunction with the second embodiment of the invention. Similarly, the scope of this embodiment also encompasses polymers wherein the central block D may be comprised of copolymers of one or more conjugated diene of formula (3) and any other anionically polymerizable monomer capable of polymerizing with the conjugated diene of formula (3).

This embodiment also encompasses polymers to be epoxidized wherein the blocks A are prepared by, initially, polymerizing at least one aryl-substituted olefin alone, and, subsequently, reacting the resulting poly-aryl-substituted olefin with any compounds which, after chemical reaction with the poly-aryl-substituted olefin, will provide the residual double bonds to the A blocks, as defined above in conjunction with the discussion of the conjugated diene of formula (1). The resulting block A will therefore have substantially the same residual unsaturation (residual double bonds) on the terminal blocks A as any other block A made in accordance with this embodiment.

After the polymerization is completed the block copolymer may be subjected to a selective hydrogenation reaction before or after epoxidation. After selective hydrogenation, the polymer, if not previously epoxidized, contains a sufficient amount of its original unsaturation in the terminal blocks I and A to provide the requisite number of epoxy groups, thereby permitting chemical crosslinking in the manner discussed below, while the middle block D contains substantially none of the original unsaturation. Generally, for a block copolymer wherein the I, D and A blocks are polymerized from any of the monomers suitable for their polymerization, discussed above, the Iodine Number for the I and A blocks after the selective hydrogenation but before epoxidation is completed is about 10 to about 100% of the Iodine Number prior to the selective hydrogenation reaction, and for the D blocks it is about 0 to about 10%, preferably about 0 to about 0.5% of the Iodine Number prior to the selective hydrogenation and epoxidation reactions. Thus, in this embodiment, the block D is also selectively hydrogenated in the same manner as discussed above, while the terminal blocks I and A retain a substantial amount of their original unsaturation for conversion to epoxy groups.

The block copolymer of this embodiment is also a liquid, and, after selective hydrogenation and epoxidation, the epoxy groups in the terminal blocks I and A of each of the triblocks provide a means of crosslinking the copolymer in the manner discussed elsewhere in this application.

Epoxidized Random Copolymers

Random copolymers of this invention prior to epoxidation have controlled amounts of unsaturation incorporated randomly in an otherwise saturated backbone. In contrast to EPDM, the level of unsaturation can be inexpensively and easily controlled, e.g., to produce polymers having Iodine Number before epoxidation of about 5 to about 100, to provide a wide variation in curing rate.

In one embodiment, the random copolymers subjected to epoxidation are polymerized from the same monomers used to polymerize the block copolymers $(I)_{x}$-$(B)_{y}$-$(I)_{x}$, i.e., from at least one conjugated diene of formula (1) and at least one conjugated diene of formula (3), both defined above, provided that the diene of formula (1) is different from the diene of formula (3). This random copolymer contains about 1.0 to about 25%, preferably about 1.0 to about 10% by mole of the polymerized conjugated diene of formula (1) and about 75 to about 99%, preferably about 90 to about 99% by mole of the polymerized conjugated diene of formula (3). Suitable conjugated dienes of formula (1) are exemplified above. The most preferred conjugated diene of formula (1) for the copolymerization of these random copolymers is isoprene. Suitable conjugated dienes of formula (3) are also exemplified above. 1,3-Butadiene is the most preferred conjugated diene of formula (3) for the polymerization of the random copolymer of this embodiment. Thus, most preferably, in this embodiment, the random copolymer is polymerized from isoprene and 1,3-butadiene, and it contains about 1 to about 20% wt. of the isoprene units and about 80 to about 99% wt. of the butadiene units. The isoprene units have primarily (i.e., about 50 to about 90% wt.) the 3,4-microstructure.

In another embodiment, the random copolymers subjected to epoxidation are polymerized from the same monomers used to polymerize the block copolymers $(A)_x$-$(D)_y$-$(A)_x$, i.e., from at least one aryl-substituted olefin, at least one conjugated diene of formula (1), and at least one conjugated diene of formula (3), providing that the conjugated diene of formula (1) is different from the conjugated diene of formula (3) used in the polymerization. The conjugated dienes of formulae (1) and (3) are defined above and the aryl-substituted olefins are also the same as those defined above. This alternative random copolymer contains about 0.3 to about 15% by mole of the aryl-substituted olefin, about 1.0 to about 25%, preferably about 1.0 to about 10%, by mole of the conjugated diene of formula (1), the remainder being the conjugated diene of formula (3).

The random copolymers are subjected before or after epoxidation to the selective hydrogenation reaction discussed above for the block copolymers, during which polymerized conjugated diene units of formula (3) are substantially completely hydrogenated, while the polymerized conjugated diene units of formula (1), if not previously epoxidized, are hydrogenated to a substantially lesser extent, i.e., to such an extent that they retain a sufficient amount of their original unsaturation for conversion to the requisite number of epoxy groups, thereby producing liquid elastomers having random unsaturation proportional to the unsaturation in the polymerized dienes of formula (1). For example, for a random copolymer polymerized from a diene of formula (1) and a different diene of formula (3), the Iodine Number before selective hydrogenation and epoxidation for the polymer is about 450. After selective hydrogenation but before epoxidation, the Iodine Number for the polymer is about 10 to about 50, with most of the unsaturation being contributed by the diene of formula (1).

Similarly, for a random copolymer of an aryl-substituted olefin, a conjugated diene of formula (1) and a conjugated diene of formula (3), different from the conjugated diene of formula (1), the Iodine Number before selective hydrogenation and epoxidation of the polymer is about 250 to about 450. After selective hydrogenation but before epoxidation, the Iodine Number for the polymer is about 10 to about 100, most of it being contributed by the diene of formula (1).

Epoxidized Star-Branched Polymers

The invention is also directed to epoxidized star-branched block and random polymers.

The star-branched block polymers prior to epoxidation are made from any combination of blocks I and B, A and D, or I, D and A all defined above, providing that each free end (i.e., the uncoupled end) of the star-branched polymer is either an I or an A block in the star-branched block polymers made from blocks I and B, A and D or I, D and A, respectively. The star-branched I-B block polymers comprise about 0.5 to about 25%, preferably about 1 to about 5% by wt. of the I blocks, and about 75 to about 99.5%, preferably about 95 to about 99% by wt. of the B blocks. The star-branched A-D block polymers comprise about 4 to about 60%, preferably about 8 to about 32% by wt. of the A blocks, and about 40 to about 96%, preferably about 68 to about 92% by wt. of the D blocks. The star-branched I-D-A block polymers comprise about 1 to about 15, preferably about 2 to about 8% wt. blocks I, about 2 to about 30, preferably about 4 to about 16% wt. of the blocks A and about 55 to about 97, preferably about 76 to about 94% wt. of the blocks D. The block A of this copolymer is either a block or a random copolymer of about 30 to about 70% by mole of at least one aryl-substituted olefin and about 30 to about 70% by mole of at least one conjugated diene of formula (1).

The star-branched block polymers may be selectively hydrogenated before or after epoxidation to such an extent that blocks B or D contain substantially none of the original unsaturation, while each of the blocks I and A, respectively, if not previously epoxidized retains a sufficient amount of the original unsaturation of the conjugated dienes present in these blocks for conversion to the requisite epoxy groups. Thus, for the I-B star-branched block polymer, after the selective hydrogenation reaction but before epoxidation, the Iodine Number for the I blocks is about 10 to about 100%, preferably about 25 to about 100%, and more preferably about 50 to about 100% of the Iodine Number prior to the selective hydrogenation and epoxidation reaction, and for the B blocks it is about 0 to about 10%, preferably about 0 to about 0.5% of the Iodine Number prior to the selective hydrogenation reaction. Similarly, for the A-D star-branched block polymer, after the selective hydrogenation reaction but before epoxidation, the Iodine Number for the A blocks is about 10 to about 100%, preferably about 25 to about 100%, more preferably about 50 to about 100% of the Iodine Number prior to the selective hydrogenation and epoxidation reactions, and for the D blocks it is about 0 to about 10%, preferably about 0 to about 0.5% of the Iodine Number prior to selective hydrogenation. Similarly, for the I-D-A star-branched block polymer, the Iodine Number for each of the I and A blocks after the selective hydrogenation is completed is about 10 to about 100% of the Iodine Number prior to the selective hydrogenation and epoxidation reactions, and for the D blocks it is about 0 to about 10%, preferably about 0 to about 0.5% of the Iodine Number prior to selective hydrogenation. Thus, in this embodiment, the block D is also selectively hydrogenated in the same manner as discussed above for the central blocks B and D of the other embodiments of the invention.

The star-branched random polymers prior to epoxidation are made from any combination of at least one diene of formula (1) and at least one diene of formula (3), different from the diene of formula (1), or from any combination of at least one aryl-substituted olefin, at least one diene of formula (1) and at least one diene of formula (3), different from the diene of formula (1), all of which are the same as those discussed above. The star-branched random polymers of the dienes of formulae (1) and (3), which must be different from each other, comprise about 1 to about 25%, preferably about 1 to about 10% by wt. of the diene of formula (1) and about 75 to about 99%, preferably about 90 to about 99% by wt. the diene of formula (3). The star-branched random polymers of the aryl-substituted olefin and the dienes of formulae (1) and (3) comprise about 0.3 to about 15% by mole of the aryl-substituted olefin, about 1 to about 25%, preferably about 1 to about 10% by mole of the conjugated diene of formula (1), and the remainder of the conjugated diene of formula (3). The star-branched random polymers may also be selectively hydrogenated to such an extent that the polymerized dienes of formula (3) contain substantially none of the original unsaturation, while the polymerized diene units of formula (1), if not previously epoxidized, retain a sufficient amount of the original unsaturation for conversion to the requisite number of epoxy groups. Thus, for the star-branched random polymer of the conjugated diene of formula (1) and a different diene of formula (3), both identified above, the Iodine Number for the polymerized diene of formula (1), after the selective hydrogenation, but before epoxidation, is about 10 to about 100%, preferably about 25 to about 100%, and more preferably about 50 to about 100% of the Iodine Number prior to the selective hydrogenation and epoxidation reactions, and for the polymerized diene of formula (3) it is about 0 to about 10%, preferably about 0 to about 0.5% of the Iodine Number prior to selective hydrogenation. Similarly, for the star-branched random polymers made from at least one aryl-substituted olefin, at least one diene of formula (1) and at least one diene of formula (3), the Iodine Number for the polymerized diene of formula (1), after selective hydrogenation but before epoxidation, is about 10 to about 100%, preferably about 25 to about 100%, and more preferably about 50 to about 100% of the Iodine Number prior to the selective hydrogenation and epoxidation reactions, and for the polymerized diene of formula (3) it is about 0 to about 10%, preferably about 0 to about 0.5% of the Iodine Number prior to selective hydrogenation Polymerization Reaction The block copolymers which are subjected to epoxidation and in most cases to selective hydrogenation in accordance with this invention are prepared by any known block polymerization processes, preferably by an anionic polymerization process. Anionic polymerization is well known in the art and it is utilized in the production of a variety of commercial polymers. An excellent comprehensive review of the anionic polymerization processes appears in the text ADVANCES IN POLYMER SCIENCE 56, ANIONIC POLYMERIZATION, pp. 1–90, Springer-Verlag, Berlin, Heideberg, New York, Tokyo 1984 in a monograph entitled ANIONIC POLYMERIZATION OF NON-POLAR MONOMERS INVOLVING LITHIUM, by R. N. Young, R. P. Quirk and L. J. Fetters, incorporated herein by reference. The anionic polymerization process is conducted in the presence of a suitable anionic catalyst (also known as an initiator), such as n-butyl-lithium, sec-butyl-lithium, t-butyl-lithium, sodium naphthalide or cumyl potassium. The amount of the catalyst and the amount of the monomer in the polymerization reaction dictate the molecular weight of the polymer. The polymerization reaction is conducted in solution using an inert solvent as the polymerization medium, e.g., aliphatic hydrocarbons, such as hexane, cyclohexane or heptane, or aromatic solvents, such as benzene or toluene. In certain instances, inert polar solvents, such as tetrahydrofuran, can be used alone as a solvent, or in a mixture with a hydrocarbon solvent.

The block polymerization process will be exemplified below for the polymerization of the first embodiment of the invention, i.e., a triblock of polyisoprene-polybutadiene-polyisoprene which is subsequently epoxidized. However, it will be apparent to those skilled in the art that the same process principles can be used for the polymerization of all copolymers of the invention.

The process, when using a lithium-based catalyst, comprises forming a solution of the isoprene monomer in an inert hydrocarbon solvent, such as cyclohexane, modified by the presence therein of one or more polar compounds selected from the group consisting of ethers, thioethers and tertiary amines, e.g., tetrahydrofuran. The polar compounds are necessary to control the microstructure of the butadiene center block, i.e., the content of the 1,2-structure thereof. The higher the content of the polar compounds, the higher will be the content of the 1,2-structure in these blocks. Since the presence of the polar compound is not essential in the formation of the first polymer block with many initiators unless a high 3,4-structure content of the first block is desired, it is not necessary to introduce the polar compound at this stage, since it may be introduced just prior to or together with the addition of the butadiene in the second polymerization stage. Examples of polar compounds which may be used are dimethyl ether, diethyl ether, ethyl methyl ether, ethyl propyl ether, dioxane, diphenyl ether, tripropyl amine, tributyl amine, trimethyl amine, triethyl amine, and N-,N-,N'-,N'-tetramethyl ethylene diamine. Mixtures of the polar compounds may also be used. The amount of the polar compound depends on the type of the polar compound and the polymerization conditions as will be apparent to those skilled in the art. The effect of polar compounds on the polybutadiene microstructure is detailed in ANTKOWIAK et al, TEMPERATURE AND CONCENTRATION EFFECTS ON POLAR-MODIFIED ALKYL LITHIUM POLYMERIZATIONS AND COPOLYMERIZATIONS, JOURNAL OF POLYMER SCIENCE: Part A-1, Vol. 10, 1319–1334 (1972), incorporated herein by reference. The polar compounds also accelerate the rate of polymerization. If monomers other than 1,3-butadiene, e.g., pentadiene, are used to polymerize the central blocks B or D, polar compounds are not necessary to control the microstructure because such monomers will inherently produce polymers which do not possess crystallinity after hydrogenation.

When the alkyl lithium-based initiator, a polar compound and an isoprene monomer are combined in an inert solvent, polymerization of the isoprene proceeds to produce the first terminal block whose molecular weight is determined by the ratio of the isoprene to the initiator. The "living" polyisoprenyl anion formed in this first step is utilized as the catalyst for further polymerization. At this time, butadiene monomer is introduced into the system and block polymerization of the second block proceeds, the presence of the polar compound now influencing the desired degree of branching (1,2-structure) in the polybutadiene block. The resulting product is a living diblock polymer having a terminal anion and a lithium counterion. The living diblock polymer serves as a catalyst for the growth of the final isoprene block, formed when isoprene monomer is again added to the reaction vessel to produce the final polymer block, resulting in the formation of the I-B-I triblock. Upon completion of polymerization, the living anion, now present at the terminus of the triblock, is destroyed by the addition of a proton donor, such as methyl alcohol or acetic acid. The polymerization reaction is usually conducted at a temperature of between 0° C. and about 100° C., although higher temperatures can be used. Control of a chosen reaction temperature is desirable since it can influence the effectiveness of the polar compound additive in controlling the polymer microstructure. The reaction temperature can be, for example, from 50° to 80° C. The reaction pressure is not critical and varies from atmospheric to about 100 psig.

If the polar compounds are utilized prior to the polymerization of the first I segment, I blocks with high 3,4-unit content are formed. If polar compounds (some of which can be Lewis bases) are added after the initial I segment is prepared, the first I segment will possess a high percentage of 1,4-microstructure (which is trisubstituted), and the second I segment will have a high percentage of 3,4-microstructure.

The production of triblock polymers having a high 1,4-unit content on both of the terminal I blocks is also possible by the use of coupling techniques illustrated below for a polyisoprene-polybutadiene-polyisoprene block copolymer:

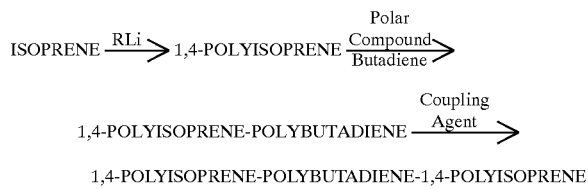

The substitution of myrcene for the isoprene during the polymerization of the I blocks insures the incorporation of a high proportion of trisubstituted double bonds, even in the presence of polar compounds since myrcene contains a pendant trisubstituted double bond which is not involved in the polymerization process. In a coupling process, similar to that described above, block polymers containing polyisoprene end blocks (or any other polymerized monomer suitable for use in the I block) having a high 3,4-microstructure content can be obtained by adding the polar compound prior to the isoprene (or another monomer) polymerization.

The use of the coupling technique for the production of triblock polymers reduces the reaction time necessary for the completion of polymerization, as compared to sequential addition of isoprene, followed by butadiene, followed by isoprene. Such coupling techniques are well known and utilize coupling agents, such as esters, $CO_2$, iodine, dihaloalkanes, silicon tetrachloride, divinyl benzene, alkyl trichlorosilanes and dialkyl dichlorosilanes. The use of tri- or tetra-functional coupling agents, such as alkyl trichlorosilanes or silicon tetrachloride, permits the formation of macromolecules having 1- or 2- main chain branches, respectively. The addition of divinyl benzene as a coupling agent has been documented to produce molecules having up to 20 or more separately joined segments.

The use of some of the coupling agents provides a convenient means of producing the star-branched block and random polymers which are subsequently epoxidized. The star-branched block polymers are made from any combination of blocks I and B, A and D or I, D and A, defined above, providing that each free end (i.e., the uncoupled end) of the star-branched polymer is either an I or an A block, respectively. The star-branched random polymers are made from any combination of at least one diene of formula (1) and at least one diene of formula (3), different from the diene of formula (1), or from at least one aryl-substituted olefin, at least one diene of formula (1) and at least one diene of formula (3), different from the diene of formula (1). The molecular weight of the star-branched block and random copolymers will depend on the number of branches in each such copolymer, as will be apparent to those skilled in the art. Suitable coupling agents and reactions are disclosed in the following references which are incorporated herein by reference: U.S. Pat. Nos. 3,949,020; 3,594,452; 3,598,887; 3,465,065; 3,078,254; 3,766,301; 3,632,682; 3,668,279; and Great Britain patents 1,014,999; 1,074,276; 1,121,978.

The random copolymers which are subjected to epoxidation in accordance with this invention are polymerized and/or coupled in a similar fashion, but all monomers, e.g., isoprene and butadiene, are mixed in a proper ratio prior to the reaction with the polar compound-modified alkyllithium. In the random polymer preparation, of course, only one stage is necessary.

Selective Hydrogenation

The selective hydrogenation reaction will also be described below using a triblock of polyisoprene-polybutadiene-polyisoprene not previously subjected to epoxidation as an example. However, it will be apparent to those skilled in the art that any polymers of this invention can be selectively hydrogenated in the same manner.

The block copolymer is selectively hydrogenated to saturate the middle (polybutadiene) block of each of the triblocks. The method of selectively hydrogenating the polybutadiene block is similar to that of Falk, "Coordination Catalysts For The Selective Hydrogenation of Polymeric Unsaturation", JOURNAL OF POLYMER SCIENCE: PART A-1, Volume 9, 2617–2623 (1971), but it is conducted with a novel hydrogenation catalyst and process used herein. Any other known selective hydrogenation methods may also be used, as will be apparent to those skilled in the art, but it is preferred to use the method described herein. In summary, the selective hydrogenation method preferably used herein comprises contacting the previously-prepared block copolymer with hydrogen in the presence of the novel catalyst composition.

The novel hydrogenation catalyst composition and hydrogenation process are described in detail in application Ser. No. 07/466,136, filed on Jan. 16, 1990. The hydrogenation catalyst composition is synthesized from at least one transition metal compound and an organometallic reducing agent. Suitable transition metal compounds are compounds of metals of Group IVb, Vb, VIb or VIII, preferably IVb or VIII of the Periodic Table of the Elements, published in LANGE'S HANDBOOK OF CHEMISTRY (13th Edition, 1985) McGraw-Hill Book Company, New York (John A. Dean, editor). Non-limiting examples of such compounds are metal halides, e.g., titanium tetrachloride, vanadium tetrachloride; vanadium oxytrichloride, titanium and vanadium alkoxides, wherein the alkoxide moiety has a branched or unbranched alkyl radical of 1 to about 20 carbon atoms, preferably 1 to about 6 carbon atoms. Preferred transition metal compounds are metal carboxylates or alkoxides of Group IVb or VIII of the Periodic Table of the Elements, such as nickel (II) 2-ethylhexanoate, titanium isopropoxide, cobalt (II) octoate, nickel (II) phenoxide and ferric acetylacetonate.

The organometallic reducing agent is any one or a combination of any of the materials commonly employed to activate Ziegler-Natta olefin polymerization catalyst components containing at least one compound of the elements of Groups Ia, IIa, IIb, IIIa, or IVa of the Periodic Table of the Elements. Examples of such reducing agents are metal alkyls, metal hydrides, alkyl metal hydrides, alkyl metal halides, and alkyl metal alkoxides, such as alkyllithium compounds, dialkylzinc compounds, trialkylboron compounds, trialkylaluminum compounds, alkylaluminum halides and hydrides, and tetraalkylgermanium compounds. Mixtures of the reducing agents may also be employed. Specific examples of useful reducing agents include n-butyllithium, diethylzinc, di-n-propylzinc, triethylboron, diethylaluminumethoxide, triethylaluminum, trimethylaluminum, triisoutylaluminum, tri-n-hexylaluminum, ethylaluminum dichloride, dibromide, and dihydride, isobutyl aluminum dichloride, dibromide, and dihydride, diethylaluminum chloride, bromide, and hydride, di-n-propylaluminum chloride, bromide, and hydride diisobutylaluminum chloride, bromide and hydride, tetramethylgermanium, and tetraethylgermanium. Organometallic reducing agents which are preferred are Group IIIa metal alkyls and dialkyl metal halides having 1 to about 20 carbon atoms per alkyl radical. More preferably, the reducing agent is a trialkylaluminum compound having 1 to about 6 carbon atoms per alkyl radical. Other reducing agents which can be used herein are disclosed in Stevens et al, U.S. Pat. No. 3,787,384, column 4, line 45 to column 5, line 12 and in Strobel et al, U.S. Pat. No. 4,148,754, column 4, line 56 to column 5, line 59, the entire contents of both of which are incorporated herein by reference. Particularly preferred reducing agents are metal alkyl or hydride derivatives of a metal selected from Groups Ia, IIa and IIIa of the Periodic Table of the Elements, such as n-butyl lithium, sec-butyl lithium, n-hexyl lithium, phenyl-lithium, triethylaluminum, tri-isobutylaluminum, trimethylaluminum, diethylaluminum hydride diethylaluminum ethoxide, and dibutylmagnesium.

The molar ratio of the metal derived from the reducing agent to the metal derived from the transition metal compound will vary for the selected combinations of the reducing agent and the transition metal compound, but in general it is about 1:1 to about 12:1, preferably about 1.5:1 to about 8:1, more preferably about 2:1 to about 7:1 and most preferably about 2.5:1 to about 6:1. It will be apparent to those skilled in the art that the optimal ratios will vary depending upon the transition metal and the organometallic agent used, e.g., for the alkylaluminum/nickel(II) systems, the preferred aluminum: nickel molar ratio is about 2.5:1 to about 4:1, for the alkylaluminum/cobalt(II) systems, the preferred aluminum: cobalt molar ratio is about 3:1 to about 4:1 and for the alkylaluminum/titanium(IV) alkoxides systems, the preferred aluminum:titanium molar ratio is about 3:1 to about 6:1.

The mode of addition and the ratio of the reducing agent to the transition metal compound are important in the production of the novel hydrogenation catalyst having superior selectivity, efficiency and stability, as compared to prior art catalytic systems. During the synthesis of the catalysts it is preferred to maintain the molar ratio of the reactants used to synthesize the catalyst substantially constant. This can be done either by the addition of the reducing agent, as rapidly as possible, to a solution of the transition metal compound, or by a substantially simultaneous addition of the separate streams of the reducing agent and the transition metal compound to a catalyst synthesis vessel in such a manner that the selected molar ratios of the metal of the reducing agent to the metal of the transition metal compound are maintained substantially constant throughout substantially the entire time of addition of the two compounds. The time required for the addition must be such that excessive pressure and heat build up are avoided, i.e., the temperature should not exceed about 80° C. and the pressure should not exceed the safe pressure limit of the catalyst synthesis vessel.

In a preferred embodiment, the reducing agent and the transition metal compound are added substantially simultaneously to the catalyst synthesis vessel in such a manner that the selected molar ratio of the reducing agent to the transition metal compound is maintained substantially constant during substantially the entire time of the addition of the two compounds. This preferred embodiment permits the control of the exothermic reaction so that the heat build up is not excessive, and the rate of gas production during the catalyst synthesis is also not excessive-accordingly the gas build-up is relatively slow. In this embodiment, carried out with or without a solvent diluent, the rate of addition of the catalyst components is adjusted to maintain the synthesis reaction temperature at or below about 80° C., which promotes the formation of the selective hydrogenation catalyst. Furthermore, the selected molar ratios of the metal of the reducing agent to the metal of the transition metal compound are maintained substantially constant throughout the entire duration of the catalyst preparation when the simultaneous mixing technique of this embodiment is employed.

In another embodiment, the catalyst is formed by the addition of the reducing agent to the transition metal compound. In this embodiment, the timing and the order of addition of the two reactants is important to obtain the hydrogenation catalyst having superior selectivity, efficiency and stability. Thus, in this embodiment, it is important to add the reducing agent to the transition metal compound in that order in as short a time period as practically possible. In this embodiment, the time allotted for the addition of the reducing agent to the transition metal compound is critical for the production of the novel catalyst. The term "as short a time period as practically possible" means that the time of addition is as rapid as possible, such that the reaction temperature is not higher than about 80° C. and the reaction pressure does not exceed the safe pressure limit of the catalyst synthesis vessel. As will be apparent to those skilled in the art, that time will vary for each synthesis and will depend on such factors as the types of the reducing agents, the transition metal compounds and the solvents used in the synthesis, as well as the relative amounts thereof, and the type of the catalyst synthesis vessel used. For purposes of illustration, a solution of about 15 ml of triethylaluminum in hexane should be added to a solution of nickel(II) octoate in mineral spirits in about 10–30 seconds. Generally, the addition of the reducing agent to the transition metal compound should be carried out in about 5 seconds (sec) to about 5 minutes, depending on the quantities of the reagents used. If the time period during which the reducing agent is added to the transition metal compound is prolonged, e.g., more than 15 minutes, the synthesized catalyst is less selective, less stable and may be heterogeneous.

In the embodiment wherein the reducing agent is added as rapidly as possible to the transition metal compound, it is also important to add the reducing agent to the transition metal compound in the aforementioned sequence to obtain the novel catalyst. The reversal of the addition sequence, i.e., the addition of the transition metal compound to the reducing agent, or the respective solutions thereof, is detrimental to the stability, selectivity, activity and homogeneity of the catalyst and is therefore undesirable.

In all embodiments of the hydrogenation catalyst synthesis, it is preferred to use solutions of the reducing agent and the transition metal compound in suitable solvents, such as hydrocarbon solvents, e.g., cyclohexane, hexane, pentane, heptane, benzene, toluene or mineral oils. The solvents used to prepare the solutions of the reducing agent and of the transition metal compound may be the same or different, but if they are different, they must be compatible with each other so that the solutions of the reducing agent and the transition metal compound are fully soluble in each other.

The hydrogenation process comprises contacting the unsaturated polymer to be hydrogenated with an amount of the catalyst solution containing about 0.1 to about 0.5, preferably about 0.2 to about 0.3 mole percent of the transition metal based on moles of the polymer unsaturation. The hydrogen partial pressure is about 5 psi to about several hundred psi, but preferably it is about 10 to about 100 psi. The temperature of the hydrogenation reaction mixture is about 25 to about 80° C., since higher temperatures may lead to catalyst deactivation. The length of the hydrogenation reaction may be as short as 30 minutes and, as will be apparent to those skilled in the art, depends to a great extent on the actual reaction conditions employed. The hydrogenation process may be monitored by any conventional means, e.g., infra-red spectroscopy, hydrogen flow rate, total hydrogen consumption, or any combination thereof.

Upon completion of the hydrogenation process, unreacted hydrogen is either vented or consumed by the introduction of the appropriate amount of an unsaturated material, such as 1-hexene, which is converted to an inert hydrocarbon, e.g., hexane. Subsequently, the catalyst is removed from the resulting polymer solution by any suitable means, selected depending on the particular process and polymer. For a low molecular weight material, for example, catalyst residue removal may consist of a treatment of the solution with an oxidant, such as air, and subsequent treatment with ammonia and optionally methanol in amounts equal to the molar amount of the metals (i.e., the sum of the transition metal and the metal of the reducing agent) present in the hydrogenation catalyst to yield the catalyst residues as a filterable precipitate, which is filtered off. The solvent may then be removed by any conventional methods, such as vacuum stripping, to yield the product polymer as a clear, colorless fluid.

Alternatively, and in a preferred embodiment, upon completion of the hydrogenation reaction, the mixture is treated with ammonia in the molar amount about equal to that of the metals (i.e., the sum of the transition metal and the metal of the reducing agent) and aqueous hydrogen peroxide, in the molar amount equal to about one half to about one, preferably one half, of the amount of the metals. Other levels of the ammonia and peroxide are also operative, but those specified above are particularly preferred. In this method, a precipitate forms, which may be filtered off as described above.

In yet another alternative method, the catalyst may be removed by extraction with an aqueous mineral acid, such as sulfuric, phosphoric or hydrochloric acid, followed by washing with distilled water. A small amount of a material commonly used as an aid in removing transition metal-based catalysts, such as a commercially available high molecular weight diamine, e.g., Jeffamine D-2000 from Texaco, may be added to aid in phase separation and catalyst removal during the extractions. The resultant polymer solution is then dried over a drying agent, such as magnesium sulfate, separated from the drying agent and the solvent is then separated by any conventional methods, such as vacuum stripping, to yield a polymer as a clear fluid. Other methods of polymer isolation, such as steam or alcohol flocculation, may be employed depending upon the hydrogenated polymer properties.

Until the instant invention, epoxidized liquid hydrocarbon elastomers have not been produced which have the capability of maintaining a large distance between crosslinks (high $M_c$) after curing. Our invention provides epoxidized block hydrocarbon polymers capable of being cured to a perfect network with a distance between crosslinks substantially equivalent to the dimensions of the uncured elastomeric molecule. In addition to the expected improvements in elastomeric properties, the saturated main chain of the polymers of our invention provides a high degree of oxidative and thermal stability. Unique materials can also be obtained by chemical modifications of the epoxidized block polymers of this invention, since such modifications can be carried out selectively only at the epoxidized terminal ends of the molecules.

The crosslinking of the epoxidized, and optionally, selectively hydrogenated block polymers of this invention is conducted in a conventional manner by contacting the block copolymer with a suitable crosslinking agent or a combination of such agents. The crosslinking process produces a copolymer having uniform distance between cross-links.

The epoxidized random copolymers may also be cross-linked in the same manner as the block copolymers.

Epoxidation Reaction

The liquid block or random elastomeric copolymer may be epoxidized by such conventional and well-known means as described in U.S. Pat. No. 3,448,174. Thus, the starting copolymer may be subjected to the action of any suitable conventional epoxidizing agent. Conveniently the epoxidation is carried out in solution in a conventional inert volatile organic solvent for the copolymer. For example, the solvent may be a hydrocarbon, such as an aliphatic or cycloaliphatic hydrocarbon, e.g., hexane, cyclohexane, etc., or an aromatic hydrocarbon e.g., benzene, toluene, and the like, or a halogen-substituted hydrocarbon, e.g., methylene chloride or dichloroethylene. The concentration of the copolymer in the solvent is in no way critical, and it may be mentioned by way of non-limiting example, that solutions containing 5% or less to 40% or more may be used. The epoxidizing agent is frequently a peroxy acid, especially an organic peroxy acid, either aliphatic, as in peracetic acid, or aromatic, as in perbenzoic acid or m-chloroperbenzoic acid. The reaction conditions are not critical. The reaction proceeds at room temperature, but heat (e.g., 50°–150° C. or higher) may be applied if desired to speed it up. The amount of epoxidizing agent is not critical, and the optimum amount in any given case will depend upon such variables as the particular epoxidizing agent used, the degree of epoxidation desired, the particular starting copolymer used (especially its degree of unsaturation), and the like. The amount of epoxidizing agent may be roughly equivalent to the unsaturation in the starting copolymer as determined by iodine number, although smaller amounts, e.g., 0.1 molar equivalent (especially when only partial epoxidation is desired), may of course also be used. No special manipulation of the reaction mixture is necessary; for example, it is sufficient to simply stir the mixture, say for a period of 2–24 hours. The resulting epoxidized polymer may be recovered from the reaction solution in any suitable manner, for example by precipitating it with a non-solvent (e.g., ethanol or water) or by evaporation of the solvent. The infrared spectrum of the dried epoxidized copolymer shows absorption due to epoxide (about 837 cm.$^{-1}$), and when the amount of epoxidizing agent is equivalent to the unsaturation in a selectively hydrogenated copolymer, essentially no residual absorption due to unsaturation. A solution of the epoxidized copolymer is gelled immediately by the addition of boron trifluoride, whereas before treatment with the peroxy acid, no gelation is effected by $BF_3$.

Cross-linking and Subsequent Reactions

The epoxy groups in the epoxidized copolymer render such copolymer curable or cross-linkable by conventional means such as disclosed, for example in U.S. Pat. No. 3,448,174. Such means include, for example treatment with any of the various reagents known to be effective with polymers containing epoxy groups, e.g., $BF_3$, $BF_3$ complexes, $AlCl_3$, $AlBr_3$, $SnCl_4$, etc., mineral acids (HCl, HBr, $H_2SO_4$, etc.), and carboxylic acids such as maleic, adipic, phthalic, etc. These reagents may be used to cure the epoxidized copolymer in the neat state or in solution if added in amounts less than equivalent to the epoxy groups. If these acids are added in amounts more than equivalent to the epoxy groups, the gelation will be suppressed in favor of a ring opening reaction. Thus, solution or cements can be gelled (cured) rapidly with a reagent such as boron trifluoride even at room temperature. Valuable casting, coating and sealing compositions are obtainable in this way.

In addition to use of the foregoing reagents, the epoxidized copolymers may be cured by radiation cross-linking using techniques well-known in the art which employ any of a wide variety of electron beam or electromagnetic wavelengths, e.g., alpha, beta, gamma, X-rays and high energy electrons or non-ionizing radiation such as ultraviolet, visible, infrared, microwave or radio frequency.

The cross-linked epoxidized polymers of this invention are useful in adhesive, sealing and caulking compositions.

The epoxidized copolymers of this invention may also be hydroxylated by methods old in the art as disclosed, for example, in U.S. Pat. No. 3,448,174, such as by treating it with an acidic agent such as HCl to open the epoxy rings. The resulting hydroxylated copolymer may then be cured by agents such as diisocyanates, e.g., toluene diisocyanate, or a dianhydride such as pyromellitic anhydride. Alternatively, the hydroxylated copolymer may be maleated by treatment with maleic anhydride and the maleated copolymer cured with, for example, a diisocyanate, metal oxide or diamine. As an alternative to direct curing, the maleated copolymer may be mixed with a suitable monomer such as styrene or certain acrylic esters to form a casting liquid or paste or an adhesive which may be further polymerized with the aid of a free radical initiator.

In addition to the foregoing reactions the epoxy groups of the epoxidized copolymers of this invention are susceptible to a wide variety of additional reactions so that the polymer chain can be modified into a great number of functional groups. Typical examples of such reactions are listed in Volume I of Heterocyclic Compounds (edited by R. C. Elderfield), John Wiley & Sons, Inc., New York, 1950, Chapter 1.

The following examples further illustrate the invention. However, it will be apparent to those skilled in the art that the specific reactants and reaction conditions used in the examples do not limit the scope of the invention.

In all of the following examples, the experimental procedures used to prepare the liquid copolymer subsequently subjected to epoxidation were performed with dried reactors and equipment and under strictly anaerobic conditions. Extreme care must be used to exclude air, moisture and other impurities capable of interfering with the delicate chemical balance involved in the synthesis of the polymers subjected to epoxidation under this invention, as will be apparent to those skilled in the art.

EXAMPLE I

This example describes the preparation of a partially epoxidized low molecular weight triblock polymer having two terminal polyisoprene blocks and a central polybutadiene block.

Cyclohexane (150 ml), which had been previously dried by storage over 4A molecular sieve, was added to a 300 ml cappable pressure bottle which had been oven dried and cooled under a nitrogen stream. The bottle was then capped with a metal cap containing several small holes and a rubber spacer. A small amount of 2-vinylpyridine (about 0.1 ml., as a 0.1 molar solution in cyclohexane) was injected through the rubber septum. This reagent acts as an indicator which signifies the presence of carbanions during titration of the solution with butyl lithium (BuLi). Next, 1.03 ml of tetramethyl ethylenediamine (TMEDA) were injected into the solution. This reagent decreases the amount of 1,4-adduct produced during the polymerization of both isoprene and butadiene blocks. The solution was titrated slowly by dropwise injection of a 1.6 molar solution of n-butyllithium until a faint yellow-orange color persisted. Then, 4.3 ml of the same n-butyllithium solution (1.6 molar) were injected to act subsequently as the polymerization catalyst.

Next, 4.63 g (6.81 ml) of isoprene which had been previously titrated as above to remove impurities, were injected into the pressure bottle which was placed in a bath heated to 50° C. and allowed to react for 4.5 hours. The thus formed polyisoprene anion acts as a catalyst for the subsequent block growth. Thirty-four grams of butadiene were pressured into a similar bottle and 2 ml of 1.0 normal triethyl aluminum were added to destroy impurities. The butadiene was distilled from its container via a cannula into the polyisoprenyl anion solution and reacted for 24 hours at 50° C. The original addition of isoprene (4.63 g) was repeated to produce a second isoprene block and complete the formation of the triblock polymer. After polymerization was complete, 0.3 ml of acetic acid were injected to terminate the polymerization by acidification of the living anion. The resultant solution was filtered through a bed of alumina to remove catalyst residues, and the solvent was removed by evaporation to give 40.8 grams of a clear viscous liquid (theoretical molecular weight=6220). Infrared analysis showed strong absorptions at 965 $cm^{-1}$ (trans polybutadiene), 890 $cm^{-1}$ (3,4-polyisoprene) and 910, 990 $cm^{-1}$ (1,2-polybutadiene).

The foregoing triblock polymer was partially epoxidized using the following procedure.

To a solution of 4.05 grams of such triblock polymer, in 100 ml of methylene chloride were added 1.44 grams of 70% metachloroperbenzoic acid dissolved in 80 ml methylene chloride. The mixture was stirred overnight at room temperature and then washed 4 times with a 5% aqueous solution of sodium bicarbonate. The organic layer was separated, dried by the addition of magnesium sulfate, filtered and concentrated by evaporation of the solvent to isolate the epoxidized polymer. Theoretically, each polymer molecule contained about 9 epoxide units.

EXAMPLE II

This example illustrates the epoxidation of a selectively hydrogenated low molecular weight triblock copolymer having two terminal polyisoprene blocks and a central polybutadiene block.

Using the procedures of Falk, J. Poly. Sci., 9, 2617–2623 (1971), a hydrogenation catalyst was prepared by reacting triethyl aluminum and cobalt octoate in cyclohexane to give a product which was 0.081 molar in cobalt and having an Al/C ratio of 3.45.

In a Parr pressure bottle which had been cleaned, dried and maintained under a $N_2$ atmosphere were added consecutively nine grams of the triblock polymer from Example I before epoxidation, 150 ml of dry cyclohexane and, 30 ml of the above described catalyst solution. The sealed bottle was flushed several times with hydrogen, heated to 50° C. and pressured to 40 psig with hydrogen. Hydrogen uptake was rapid as evidenced by a drop in pressure. The hydrogen pressure was periodically adjusted up to 40 psig. After 3 hours of reaction, hydrogen uptake had dramatically reduced and reaction was terminated. Infrared analysis of the purified, isolated product disclosed no residual double bond absorptions at 910, 965 or 990 $cm^{-1}$ originally present in the polybutadiene center block. The relatively strong residual absorption at 890 $cm^{-1}$ demonstrated the presence of unhydrogenated 3,4-polyisoprene structures available for subsequent epoxidation.

Using procedures identical to those described in Example I, 4.0 grams of the foregoing selectively hydrogenated triblock was epoxidized by reaction with 1.44 grams of 70% metachloroperbenzoic acid in methylene chloride. After the same work up, a polymer which had been epoxidized primarily on the terminal unsaturated end polyisoprene blocks was isolated.

EXAMPLE III

This example illustrates the preparation of a partially epoxidized triblock polymer having two polyisoprene terminal blocks and a central polybutadiene block.

Three hundred milliliters (ml) of purified, dried cyclohexane (99.5%, Phillips Petroleum) were introduced into a six-hundred milliliter stirred glass reactor. Air was removed from the reactor under vacuum and replaced by dry nitrogen. The reactor was equipped with an air driven stirrer, a pressure gauge, thermocouple, top surface inlet valve, dip tube feeder with valve, heating-mantle and variable controller and combination nitrogen/vacuum inlet with valve. Three ml of a 0.01M solution of bipyridyl in cyclohexane, 7.3 ml (90 mmol) of tetrahydrofuran freshly distilled from benzophenone ketyl and 1.8 ml (18 mmol) of purified isoprene were injected into the reactor. The temperature of the reactor and its contents was raised to 50° C. The solution was then titrated by addition of 1.6M butyl lithium until a persistent red color was obtained. Following this, 3.75 ml of 1.6M butyl lithium was injected into the reactor in order to initiate polymerization of the isoprene. The reaction was allowed to run for one hour, after which 47.5 g of purified butadiene were pressured into the reactor at a rate such that the reaction temperature did not exceed 70° C. After one hour, the reactor pressure had returned to its initial level and the formation of the second block of the copolymer was completed. Isoprene (1.8 ml, 18 mmol) was again injected into the reactor to allow for the formation of the third and final block of the triblock polymer. After one hour, 0.35 ml of acetic acid (4.5 mmol) were injected into the reactor to quench the triblock living anion. The color of the reaction mixture changed from a dark amber to colorless immediately. The mixture was cooled to room temperature, filtered through alumina/Celite, an anti-oxidant, Irganox 1076 from Ciba-Geigy (100 ppm based on dry polymer) was added and solvent was removed under reduced pressure to yield a triblock polymer of about 8400 molecular weight as a clear, colorless, viscous fluid. Infra-red analysis (Fourier Transform) showed the butadiene center block to possess 55% (1,2) and 45% of (1,4)-microstructure.

The foregoing block copolymer is partially epoxidized using the epoxidation procedure of Example I.

EXAMPLE IV

This example is similar to that of Example III, but the scale was increased to utilize a one gallon stainless steel pressure reactor.

1500 grams of purified, dried cyclohexane (99.5%, Phillips Petroleum) were introduced into a one gallon stirred stainless steel reactor. The reactor was equipped with a stirrer, pressure gauge, thermocouple, top surface inlet, dip tube feeder with valve, variably controlled heater and heat exchange coil. Following the addition of the solvent, 50 ml (0.614 mol) of tetrahydrofuran freshly distilled from benzophenone ketyl, 43.3 ml (0.433 mol) of purified isoprene and an additional 80 g of cyclohexane were pressured into the reactor. The temperature of the reactor and its contents was raised to 50° C. Butyl lithium (61.2 ml of 1.5M solution, 91.8 mmol) was pressured into the reactor in order to titrate impurities and initiate polymerization of the isoprene. The reaction was allowed to run for one hour, after which 1100 ml of purified butadiene (12.65 mol) were pumped into the reactor at a rate such that the reaction temperature did not exceed 60° C. Cooling water was passed through the heat exchanger during this process to aid in the control of temperature. The butadiene feed was complete within thirty minutes. One hour later, the formation of the second block of the copolymer was complete and isoprene (43.3 ml, 0.433 mol) in 50 g of cyclohexane was again pressured into the reactor to allow for the formation of the third and final block of the triblock polymer. After one hour, the reaction mixture was cooled and discharged into a vessel containing 5.2 ml of acetic acid (90.8 mmol) to quench the triblock living anion. The mixture was filtered through alumina/Celite, an anti-oxidant (100 ppm based on dry polymer) was added and the solvent was removed under reduced pressure to yield a triblock polymer of about 8200 molecular weight as a clear, colorless, viscous fluid. Infra-red analysis (Fourier Transform) showed the butadiene center block to possess 56% (1,2)- and 44% of (1,4)-microstructure.

This block copolymer is partially epoxidized using the procedure of Example I.

EXAMPLE V

This example illustrates the relationship between the molecular weight of the triblock polymers prepared in the manner substantially the same as that of Examples III and IV prior to epoxidation and their resulting bulk viscosities.

As is apparent from the data of FIG. 1, a linear relationship exists between the molecular weight of the unhydrogenated isoprene-butadiene-isoprene polymers prepared as in Examples III and IV and the log of their room temperature bulk viscosities as measured using a Brookfield Engineering LVT viscometer operating at, for example, 0.6 rpm with spindle number 5. A similar relationship also applies to the partially epoxidized block copolymers.

EXAMPLE VI

This example illustrates the preparation of a triblock polymer wherein the terminal blocks consist of isoprene-styrene copolymers and the central block is polybutadiene. Incorporation of levels of styrene approximately comparable to those of isoprene into the end blocks is beneficial with certain end uses the final epoxidized selectively hydrogenated triblock polymer.

1400 grams of purified, dried cyclohexane (99.5%, Phillips Petroleum) were introduced into a one gallon stirred stainless steel reactor. The reactor was equipped with a stirrer, pressure gauge, thermocouple, top surface inlet, dip tube feeder with valve, variably controlled heater and heat exchange coil. Following the addition of the solvent, 88 ml (1.08 mol) of tetrahydrofuran freshly distilled from benzophenone ketyl, 21.8 ml (0.218 mol) of purified isoprene, 41.5 ml of purified styrene (0.362 mol) and an additional 50 g of cyclohexane were pressured into the reactor. The temperature of the reactor and its contents was raised to 50° C. Butyl lithium (47.0 ml of 1.6M solution, 75.2 mmol) was then pressured into the reactor in order to titrate impurities and initiate polymerization of the isoprene. The reaction was allowed to run for one hour, after which 800 ml of purified butadiene (9.20 mol) were pumped into the reactor at a rate such that the reaction temperature did not exceed 60° C. Cooling water was passed through the heat exchanger during this process to aid in the control of temperature. The butadiene feed was complete within thirty minutes. One hour later, the formation of the second block of the copolymer was complete and a mixture of isoprene (21.8 ml, 0.218 mol) and styrene (41.5 ml, 0.362 mol) in 50 g of cyclohexane was again pressured into the reactor to allow for the formation of the third and final block of the triblock polymer. After one hour, the reaction mixture was cooled and discharged into a vessel containing 4.3 ml of acetic acid (75.2 mmol) to quench the triblock living anion. The mixture was filtered through alumina/Celite, an anti-oxidant (100 ppm based on dry polymer) was added and solvent was removed under reduced pressure to yield a triblock polymer of about 8000 molecular weight as a clear, colorless viscous fluid. Infra-red analysis (Fourier Transform) showed the butadiene center block to possess 57% (1,2)- and 43% (1,4)-microstructure.

This block copolymer is partially epoxidized using the epoxidation procedure of Example I.

EXAMPLE VII

This example illustrates the preparation of an epoxidized random copolymer consisting of isoprene and butadiene wherein the isoprene proportion is completely analogous to that of the triblock material of Example III.

800 ml of purified, dried cyclohexane (99.5%, Phillips Petroleum) were introduced into a two liter stirred glass reactor. The reactor was purged several times with dry nitrogen. The reactor was equipped with an air driven stirrer, a pressure gauge, thermocouple, top surface inlet valve, dip tube feeder with valve, heat exchange coil and nitrogen inlet with valve. 5 ml of a 0.01M solution of bipyridyl in cyclohexane and 16.1 ml (198 mmol) of tetrahydrofuran freshly distilled form benzophenone ketyl were injected into the reactor. The reactor contents were titrated with 1.6M butyl lithium to a persistent red endpoint. The temperature of the reactor and its contents was raised to 50° C. and 8.3 ml of 1.6M butyl lithium (13.3 mmol) were added. A mixture of 13.3 ml of isoprene (0.133 mol) and 90.9 g of purified butadiene (1.68 mol) was then pressured into the reactor at a rate that allowed for maintaining a temperature of between 50 and 60° C. The feed was completed in about 20 minutes, after which the reaction was allowed to proceed for an additional hour. The contents were cooled and discharged into a vessel containing 0.53 ml of methanol (13 mmol) to quench the copolymer living anion. The color of the reaction mixture changed from a dark amber to colorless immediately. The mixture was filtered through alumina/Celite, an anti-oxidant (100 ppm based on dry polymer) was added and solvent was removed under reduced pressure to yield a random copolymer of about 7500 molecular weight as a clear, colorless, viscous fluid. Infra-red analysis (Fourier Transform) showed the butadiene portion to possess 60% (1,2)- and 40% (1,4)-microstructure. In general, the infra-red spectrum was essentially indistinguishable from that of the triblock material of Examples III and IV.

The foregoing random copolymer is partially epoxidized using the epoxidation procedure of Example I.

EXAMPLE VIII

This example illustrates the preparation of the selective hydrogenation catalyst used in subsequent examples.

In a clean, dry pressure bottle equipped with a magnetic stir bar, were placed 77.88 ml of pure, dry cyclohexane and 7.34 g of nickel (II) octoate (8% in mineral spirits, Mooney Chemical). The bottle was sealed with a septum and bottle cap, evacuated and refilled with dry nitrogen. The process was repeated several times. The mixture was then stirred vigorously and 14.40 ml of 1.73M triethylaluminum was added via syringe as quickly as practicable (about 15 seconds). Periodically, pressure was vented by means of a needle fitted with a valve. There was no evidence of heterogeneity in the final black reaction mixture. The catalyst solution nickel concentration was 0.1M and the molar ratio of aluminum to nickel was 3.6.

EXAMPLE IX

This example illustrates the selective hydrogenation of the central polybutadiene block followed by epoxidation of an isoprene-butadiene-isoprene triblock polymer.

250 ml of cyclohexane in which was dissolved 23 g of triblock polymer made in the manner similar to that of Example III were purged of air by evacuation followed by the introduction of dry nitrogen. This amount of polymer contained 0.403 moles of polybutadiene unsaturation. To the polymer solution was added 25 ml of a hydrogenation catalyst solution comprised of triethylaluminum and nickel (II) octoate in a 3.6:1 ratio with a nickel concentration of 0.1M in cyclohexane. The resulting mixture was placed in a Parr hydrogenation apparatus and pressured to 50 psig hydrogen. The apparatus was vented and the process repeated twice more, after which the pressure was maintained at 50 psig of hydrogen. The temperature was raised to 50° C. and the mixture was agitated vigorously. Hydrogen was fed on demand in order to maintain 50 psig in the vessel and the flow rate was monitored by means of a mass flow meter. The progress of the hydrogenation process was monitored both by Fourier Transform infra-red spectroscopy and hydrogen flow rate. An infra-red spectrum obtained at the start of the process displayed the presence of primarily the butadiene unsaturation (peaks at 995, 968 and 910 wavenumbers). After thirty minutes, butadiene vinyl unsaturation (peaks at 995 and 910 wavenumbers) was gone, the trans-(1,4)-butadiene was significantly reduced (968 wavenumbers) and the isoprene vinylidene (888 wavenumbers) was very much in evidence. After ninety minutes, all or most of the unsaturation remaining was of polyisoprene. This final point corresponds to zero hydrogen flow. Upon completion of the selective hydrogenation process, the vessel was vented and the black reaction mixture was stirred in air with ammonium hydroxide and methanol stoichiometrically equivalent to the total catalyst metal content (11.5 mmol, 0.7 ml concentrated ammonia and 0.5 ml methanol). Within several hours, the mixture had changed to a dark green color indicative of oxidized nickel. The mixture was filtered through alumina/Celite and an anti-oxidant was added in the amount equivalent to 100 ppm based on the dry polymer weight. Solvent was then removed under reduced pressure to yield the product as a clear, colorless, viscous fluid.

The foregoing selectively hydrogenated copolymer is epoxidized using the epoxidation procedure of Example I.

EXAMPLE X

This example illustrates the relationship between the molecular weight of the selectively hydrogenated triblock polymers prepared in the manner of Example IX and their resulting bulk viscosities.

Figure 2:
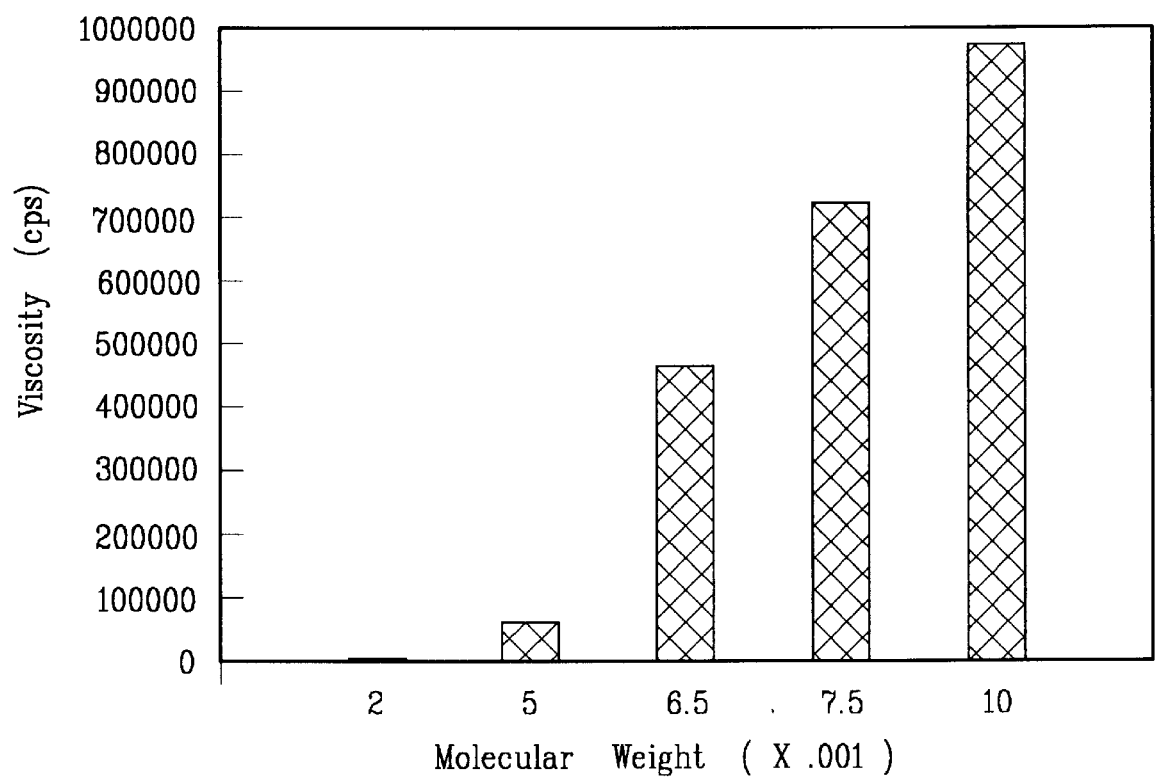
FIG. 2 shows the relationship of viscosity as a function of molecular weight for the unepoxidized but selectively hydrogenated isoprene-butadiene-isoprene triblock polymer of this invention.

As is apparent in FIG. 2, a monotonic increase in room temperature bulk viscosity is observed as the molecular weight of the selectively hydrogenated triblock polymers is increased. In all cases, a Brookfield Engineering LVT viscometer operating at, for example 0.6 rpm with spindle number 5 was used. Surprisingly, however, even at a molecular weight of ten thousand g/mol (Mn=Mw) the bulk viscosity does not exceed one million centipoises.

| Triblock Molecular Weight | | | | |
|---|---|---|---|---|
| 2000 | 5000 | 6500 | 7500 | 10000 |
| | | Bulk Viscosity (cps) | | |
| 8500 | 54700 | 424000 | 745000 | 976000 |

A similar relationship applies to the corresponding epoxidized polymers.

EXAMPLE XI

This example illustrates the selective hydrogenation of the central polybutadiene block followed by epoxidation of a triblock polymer prepared as in Example VI before epoxidation wherein the terminal blocks consist of isoprene-styrene copolymers.

The hydrogenation was carried out in a manner completely analogous to that of Example IX to give a material in which all or most of the unsaturation remaining was of polyisoprene as evidenced by Fourier Transform infra-red spectroscopy. The epoxidation is carried out using the epoxidation procedure of Example I.

EXAMPLE XII

This example illustrates the selective hydrogenation of the butadiene portion followed by epoxidation of a random copolymer of isoprene-butadiene prepared as in Example VII before epoxidation.

The hydrogenation was carried out in a manner completely analogous to that of Example IX to give a material in which only the isoprene unsaturation remained as evidenced by Fourier Transform infra-red spectroscopy. The epoxidation is carried out using the epoxidation procedure of Example I.

EXAMPLE XIII

This example illustrates the preparation of an epoxidized star-branched polymer wherein the polymer prior to epoxidation is prepared by first preparing an isoprene-butadiene-isoprene triblock living polymer that is subsequently coupled to yield branched materials containing two arms (a pentablock), three arms (Y-shaped), four arms (plus-shaped), etc. The method is similar to that of Example III, but a fractional equivalent of quenching reagent containing multiple sites to react with the polymer living anion, such as silicon tetrachloride, was employed instead of acetic acid. For example, one-fourth of an equivalent of silicon tetrachloride was used based on the amount of n-butyl lithium employed in the polymerization.

The polymers, prior to epoxidation, were colorless fluids which are partially epoxidized using the epoxidation procedure of Example I.

EXAMPLE XIV

This example illustrates the preparation of an epoxidized star-branched polymer wherein the polymer prior to epoxidation is prepared by first preparing an isoprene-butadiene diblock living polymer that is subsequently coupled to yield branched materials containing two arms (a triblock), three arms (Y-shaped), four arms (plus-shaped), etc. The method is similar to that of Example XIII, but quenching of the living anion is performed after the formation of the second polymer block, i.e., the polyisoprene-butadienyl anion. The material obtained had isoprene blocks only on the ends of the individual branches and not at their junction. The polymers are partially epoxidized using the epoxidation procedure of Example I.

EXAMPLE XV

This example illustrates the selective hydrogenation of the butadiene blocks followed by epoxidation of the branched materials of Examples XIII and XIV.

The hydrogenation was carried out in a manner analogous to that of Example IX to give materials in which most of the isoprene unsaturation remained as evidenced by Fourier Transform infra-red spectroscopy. The epoxidation is carried out using the epoxidation procedure of Example I.

It will be apparent to those skilled in the art that the specific embodiments discussed above can be successfully repeated with ingredients equivalent to those generically or specifically set forth above and under variable process conditions.

From the foregoing specification, one skilled in the art can readily ascertain the essential features of this invention and without departing from the spirit and scope thereof can adapt it to various diverse applications.

We claim:

1. An epoxidized liquid star-branched block polymer which prior to epoxidation comprises at least two alternating blocks

I-B wherein each free end of the polymer is an I block, and

I is a block of at least one polymerized conjugated diene having at least five (5) carbon atoms and the following formula

wherein $R^1$–$R^6$ are each hydrogen or a hydrocarbyl group, provided that at least one of $R^1$–$R^6$ is a hydrocarbyl group and provided that the structure of the residual double bond in the polymerized block I has the following formula

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups;

B is a block of a polymer of at least one conjugated diene, different from the diene used to polymerize the block I, having at least four (4) carbon atoms and the following formula

wherein $R^7$–$R^{12}$ are each hydrogen or a hydrocarbyl group, provided that the structure of the residual double bond in the polymerized block B has the following formula

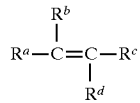
(4)

wherein $R^a$, $R^b$, $R^c$ and $R^d$ are each hydrogen (H) or a hydrocarbyl group, provided that one of $R^a$ or $R^b$ is hydrogen, one of $R^c$ or $R^d$ is hydrogen and at least one of $R^a$, $R^b$, $R^c$ or $R^d$ is a hydrocarbyl group.

* * * * *